(12) United States Patent
Nagai et al.

(10) Patent No.: US 8,103,335 B2
(45) Date of Patent: Jan. 24, 2012

(54) CARDIOGRAM WAVEFORM CORRECTING AND DISPLAYING DEVICE AND A METHOD OF CORRECTING AND DISPLAYING CARDIOGRAM WAVEFORMS

(75) Inventors: Ryuji Nagai, Suita (JP); Shinya Nagata, Suita (JP)

(73) Assignee: Nihon Kohden Corporation, Tokyo (JP)

( * ) Notice: Subject to any disclaimer, the term of this patent is extended or adjusted under 35 U.S.C. 154(b) by 1154 days.

(21) Appl. No.: 11/722,320

(22) PCT Filed: Dec. 20, 2005

(86) PCT No.: PCT/JP2005/023376
§ 371 (c)(1),
(2), (4) Date: Aug. 16, 2007

(87) PCT Pub. No.: WO2006/068145
PCT Pub. Date: Jun. 29, 2006

(65) Prior Publication Data
US 2008/0027339 A1    Jan. 31, 2008

(30) Foreign Application Priority Data

Dec. 22, 2004  (JP) .................................. 2004-370908
Jun. 27, 2005  (JP) .................................. 2005-186844

(51) Int. Cl.
*A61B 5/044* (2006.01)
(52) U.S. Cl. ........................................ 600/523; 600/509
(58) Field of Classification Search ........................ None
See application file for complete search history.

(56) References Cited

U.S. PATENT DOCUMENTS

| 5,259,387 A | 11/1993 | dePinto |
| 5,318,036 A | 6/1994 | Arand et al. |
| 5,433,208 A | 7/1995 | Lundstrom et al. |

(Continued)

FOREIGN PATENT DOCUMENTS

JP   SHO63-109103   7/1988

(Continued)

OTHER PUBLICATIONS

Sörnmo, L., "Time-Varying Filtering for Removal of Baseline Wander in Exercise ECGs," Proceedings of the Computers in Cardiology Meeting, Venice, Sep. 23-26, 1991, IEEE, Meeting 18, pp. 145-148.

(Continued)

*Primary Examiner* — Kennedy Schaetzle
(74) *Attorney, Agent, or Firm* — Jason H. Vick; Sheridan Ross PC

(57) ABSTRACT

A cardiogram waveform correcting and displaying device is disclosed that is capable of facilitating visibility of cardiogram waveforms. A first filtering system 58-1 through nth filtering system 58-*n* are low-cut filters, each having a first cutoff frequency fc1 through an nth cutoff frequency fcn, respectively. Recognition module recognizes feature values of waveforms related to variation of the waveforms in accordance with any outputs of the first filtering system 58-1 through the nth filtering system 58-*n*. Judging module 62 selects which of the first through the nth filter is used based on the recognized feature values with the recognition module. A filter which restricts base-line variation is used when the base-line variation is large, and a filter having less influence to waveforms is used when the base-line variation is small. Display controller displays on a display portion output of the selected filter.

48 Claims, 33 Drawing Sheets

U.S. PATENT DOCUMENTS

| | | | |
|---|---|---|---|
| 5,873,838 A | | 2/1999 | Mogi |
| 5,999,845 A | * | 12/1999 | dePinto .................. 600/509 |
| 6,280,391 B1 | | 8/2001 | Olson et al. |
| 6,512,944 B1 | * | 1/2003 | Kovtun et al. ............. 600/509 |
| 2004/0024327 A1 | | 2/2004 | Brodnick |

FOREIGN PATENT DOCUMENTS

| | | |
|---|---|---|
| JP | HEI3-011770 | 2/1991 |
| JP | HEI6-014896 | 1/1994 |
| JP | HEI6-261871 | 9/1994 |
| JP | HEI6-277189 | 10/1994 |
| JP | HEI6-343611 | 12/1994 |
| JP | HEI7-059738 | 3/1995 |
| JP | HEI8-024670 | 3/1996 |
| JP | HEI9-289978 | 11/1997 |
| JP | 2004-065981 | 3/2004 |
| WO | WO 92/15243 | 9/1992 |
| WO | WO 93/05574 | 3/1993 |
| WO | WO 00/46690 | 8/2000 |

OTHER PUBLICATIONS

Sörnmo, L., "Time-Varying Digital Filtering of ECG Baseline Wander," Medical and Biological Engineering and Computing, Sep. 1993, vol. 31, No. 5, pp. 503-508, Springer, Heildelberg, DE.

Extended European Search Report for European Patent Application No. 05820038, dated Jan. 15, 2010.

International Search Report (including English translation) for International (PCT) Application No. PCT/JP2005/023376, mailed Mar. 28, 2006.

Written Opinion (including English translation) for International (PCT) Application No. PCT/JP2005/023376, mailed Mar. 28, 2006.

International Preliminary Report on Patentability (including English translation) for International (PCT) Application No. PCT/JP2005/023376, issued Jun. 26, 2007.

* cited by examiner

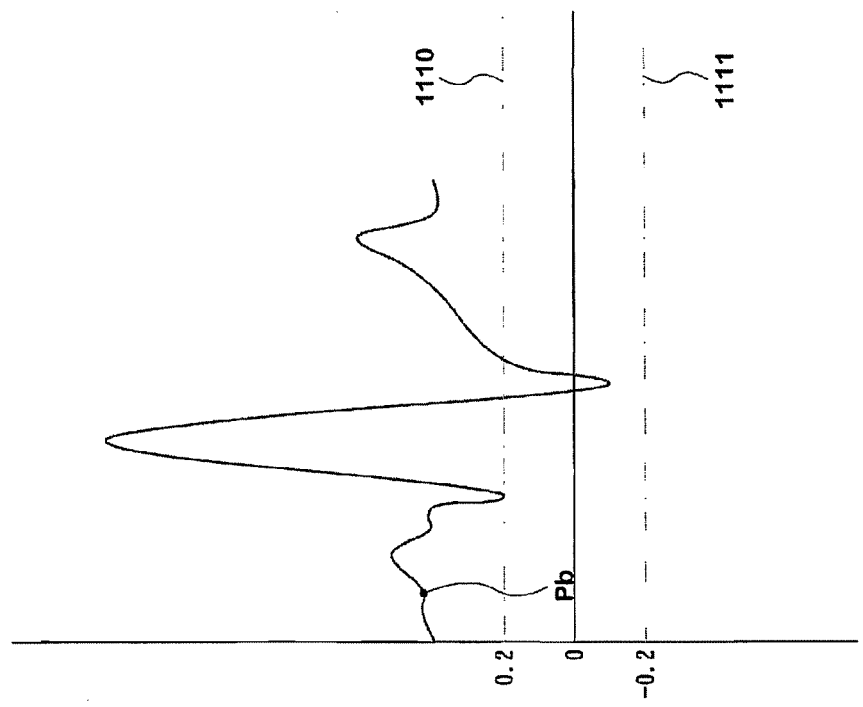
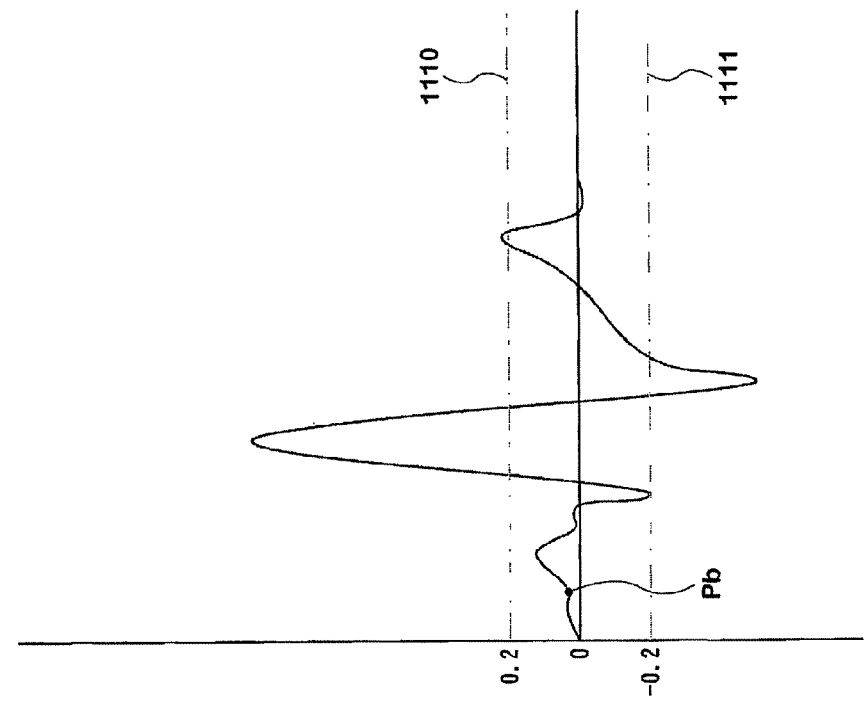

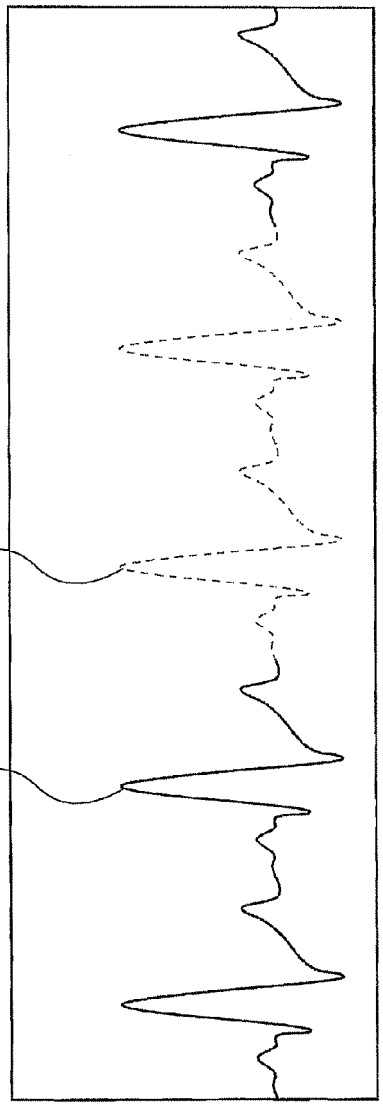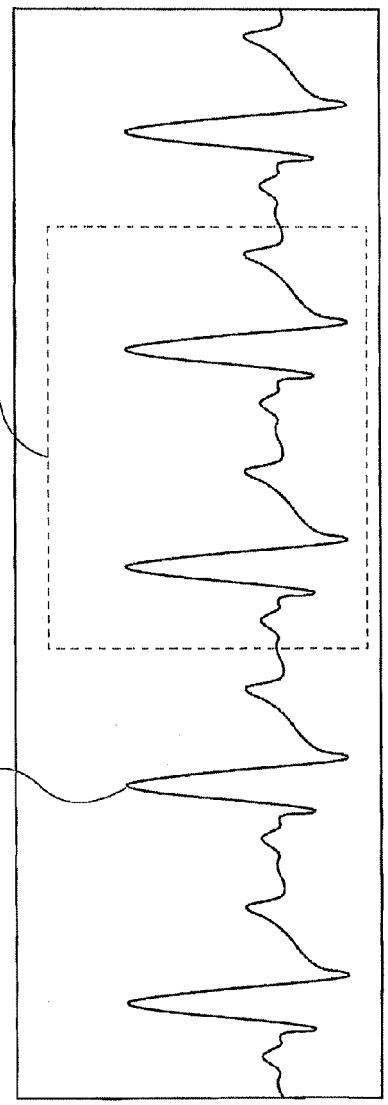
FIG.19A
FIG.19B

FIG.24

| Data No. | WAVEFORM VALUES | FEATURE POINTS | CARDIAC IDS |
|---|---|---|---|
| ⋮ | ⋮ | ⋮ | ⋮ |
| 1295 | -0.002 | Pb | 25 |
| ⋮ | ⋮ | ⋮ | ⋮ |
| 1300 | -0.001 | — | 25 |
| 1301 | 0.001 | P | 25 |
| 1302 | 0.002 | — | 25 |
| 1303 | 0.004 | — | 25 |
| ⋮ | ⋮ | ⋮ | ⋮ |
| 2050 | 0.004 | ST | 25 |
| ⋮ | ⋮ | ⋮ | ⋮ |
| 2060 | 0.009 | ST80 | 25 |
| ⋮ | ⋮ | ⋮ | ⋮ |
| 3295 | 0.001 | Pb | 27 |
| ⋮ | ⋮ | ⋮ | ⋮ |
| 3300 | 0.004 | P | 27 |
| 3301 | 0.004 | — | 27 |
| 3302 | 0.006 | — | 27 |
| 3303 | 0.005 | — | 27 |
| ⋮ | ⋮ | ⋮ | ⋮ |

FIG.25

| Data No. | WAVEFORM VALUES | CARDIAC IDS |
|---|---|---|
| ⋮ | ⋮ | ⋮ |
| 1295 | -0.002 | 25 |
| ⋮ | ⋮ | ⋮ |
| 1300 | 0.000 | 25 |
| 1301 | 0.001 | 25 |
| 1302 | 0.002 | 25 |
| 1303 | 0.003 | 25 |
| ⋮ | ⋮ | ⋮ |
| 2050 | 0.003 | 25 |
| ⋮ | ⋮ | ⋮ |
| 2060 | 0.008 | 25 |
| ⋮ | ⋮ | ⋮ |
| 3295 | 0.001 | 27 |
| ⋮ | ⋮ | ⋮ |
| 3300 | 0.003 | 27 |
| 3301 | 0.003 | 27 |
| 3302 | 0.005 | 27 |
| 3303 | 0.004 | 27 |
| ⋮ | ⋮ | ⋮ |

17a: (CARDIOGRAPH (JIS T1202) WAVEFORM OF ACCURACY
(LOW FREQUENCY CUT-OFF FREQUENCY 0.35Hz)

17b: (CARDIOGRAM MONITORING DEVICE (JIS T1304) WAVEFORM OF ACCURACY
(LOW FREQUENCY CUT-OFF FREQUENCY 0.5Hz)

17c: (LOW-EXCESSIVE RESTRICTION WAVEFORM OF ACCURACY
(LOW FREQUENCY CUT-OFF FREQUENCY 1.0Hz)

17d: (HIGH-EXCESSIVE RESTRICTION WAVEFORM OF ACCURACY
(LOW FREQUENCY CUT-OFF FREQUENCY 1.5Hz)

ORIGINAL WAVEFORM

BASE-LINE VARIATION RESTRICTION WAVEFORM

SORT OF FILTERS TO BE SELECTED FOR EACH WAVEFORM

FIG.32A ORIGINAL WAVEFORM
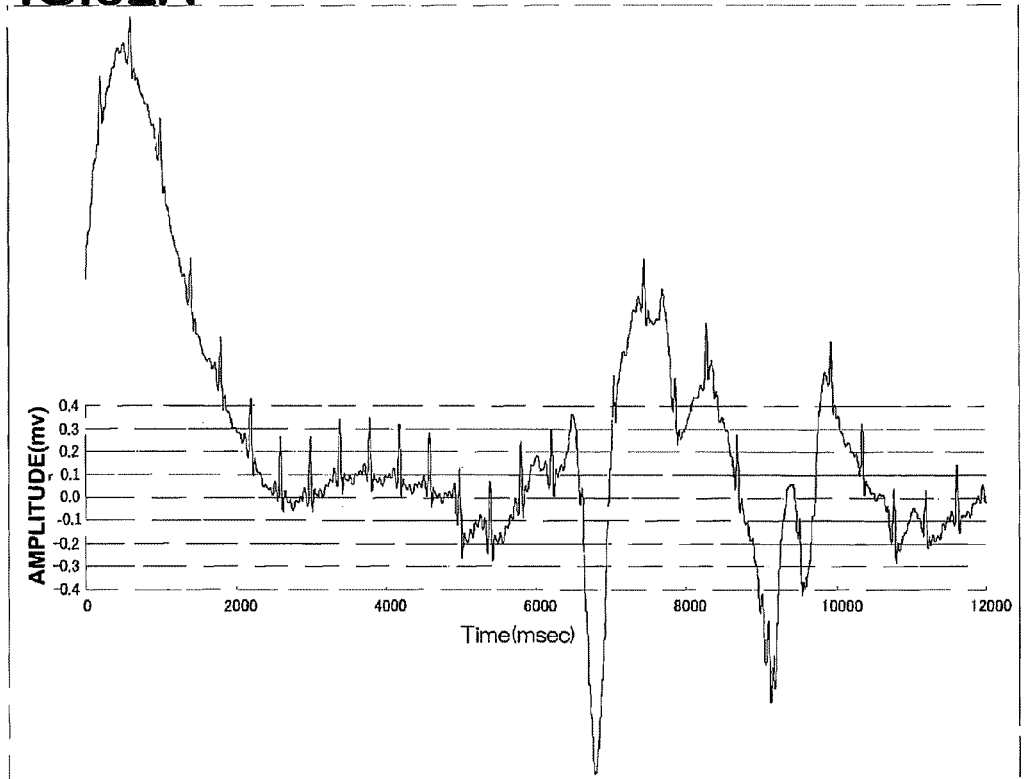
FIG.32B BASE-LINE VARIATION RESTRICTION WAVEFORM
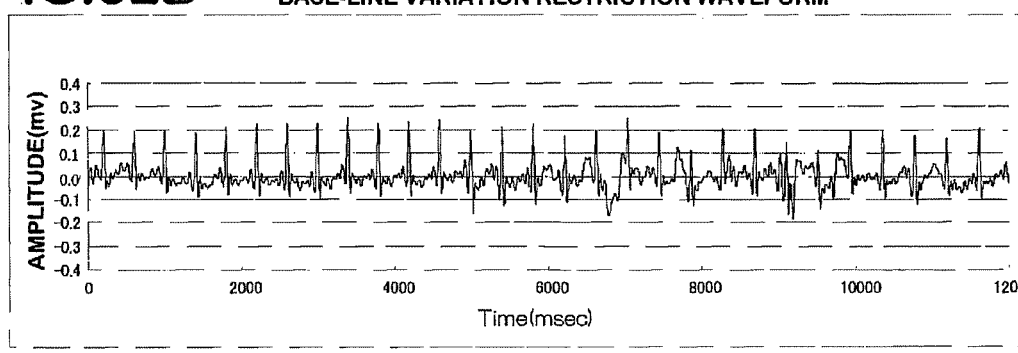
FIG.32C SORT OF FILTERS TO BE SELECTED FOR EACH WAVEFORM
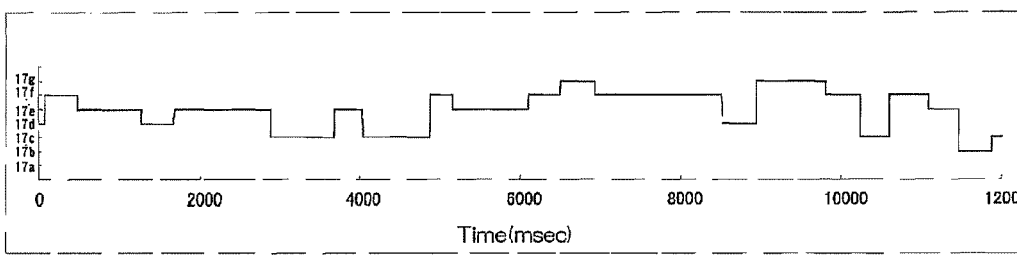

FIG.33A ORIGINAL WAVEFORM
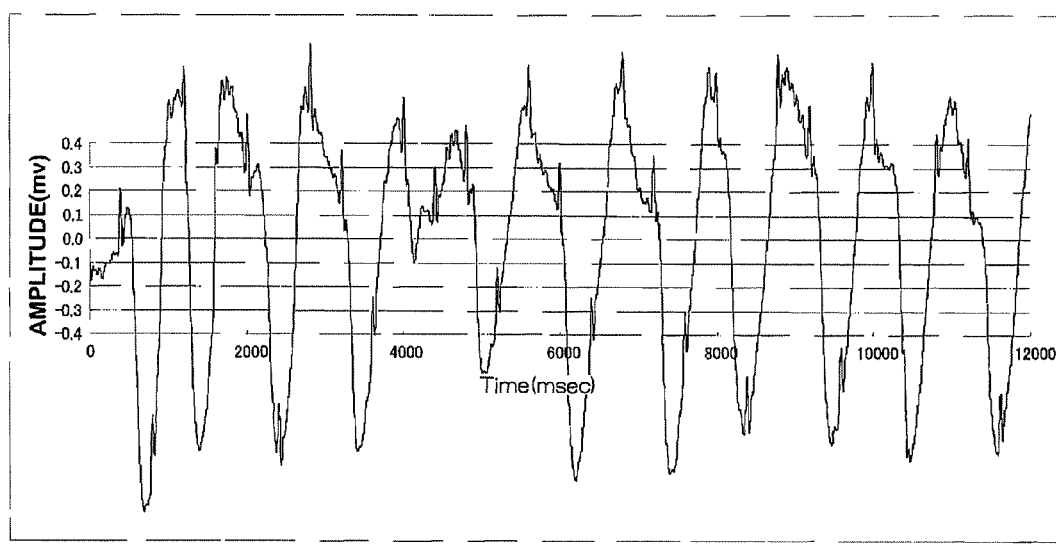
FIG.33B BASE-LINE VARIATION RESTRICTION WAVEFORM
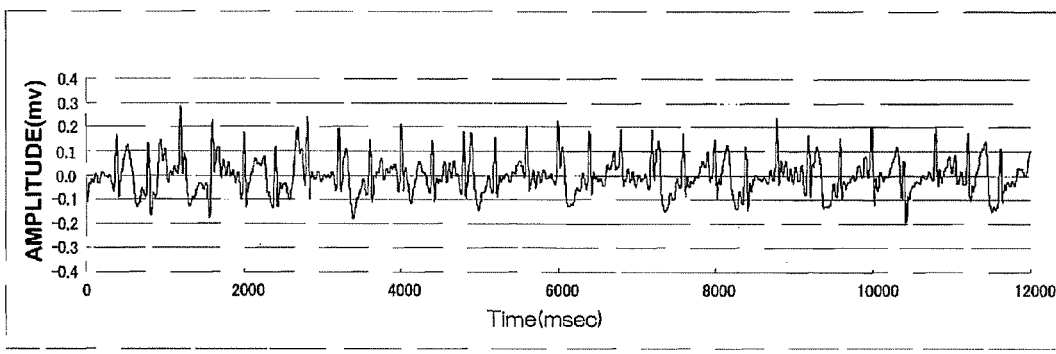
FIG.33C SORT OF FILTERS TO BE SELECTED FOR EACH WAVEFORM
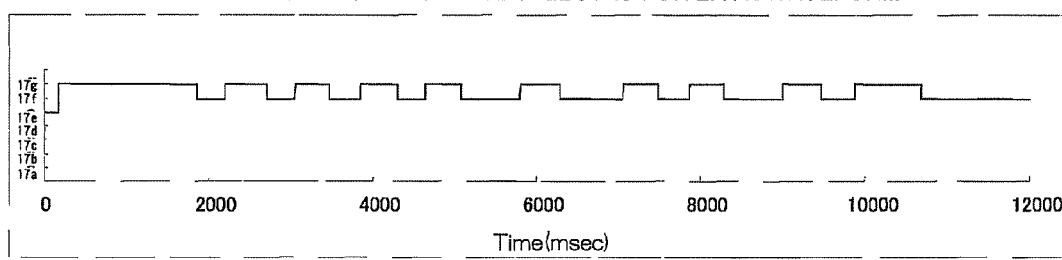

CARDIOGRAM WAVEFORM CORRECTING AND DISPLAYING DEVICE AND A METHOD OF CORRECTING AND DISPLAYING CARDIOGRAM WAVEFORMS

CROSS-REFERENCE TO RELATED APPLICATIONS

All the content disclosed in Japanese Patent Application No. 2004-370908 (filed on Dec. 22, 2004) and Japanese Patent Application No. 2005-186844 (filed on Jun. 27, 2005) including specification, claims, drawings and abstract and summary is incorporated herein by reference in its entirety.

FIELD OF THE INVENTION

The present invention relates to a cardiogram waveform correcting and displaying device and a method of correcting and displaying cardiogram waveforms. Specifically, the present invention relates to increasing visibility of a cardiogram.

BACKGROUND ART

In order to make an appropriate diagnosis of cardiac functions of a patient, display continuity for the cardiogram waveforms is required for a device that displays the cardiogram waveforms. For example, such continuity can not be maintained when the base-line of the cardiogram varies greatly by noises such as body movement of an examinee. There exists technology for maintaining display continuity of cardiogram waveforms of a cardiograph (see Patent document 1, for example). A technology by which saturation of the output from an amplifier for amplifying cardiogram signals being measured (or the input to an A/D converter) is avoided when the base-line of the cardiogram varies greatly by noises such as body movement (as disclosed in Patent document 1). Specifically, if the output of the amplifier exceeds a predetermined value, the waveform signals are made within a conversion range of the A/D converter in a short period of time by temporarily increasing a cut-off frequency of a low cut filter of a CR circuit in a cardiograph.

Patent document 1: Japanese laid-open publication No. Hei8-24670 (FIG. 1)

DISCLOSURE OF THE INVENTION

Problem to be Solved by the Invention

It is an object of the above-described Background art to make the cardiogram waveforms at a vicinity of OV (measurement: volts) in a short period of time when the base-line is varied greatly. However, such technology mainly focuses on display continuity of the cardiogram waveforms, where accurate reproduction of the features of the cardiogram waveforms is not considered.

SUMMARY OF THE INVENTION

The present invention has a plurality of aspects as stated below.

(1) (2) In accordance with characteristics of the present invention, there is provided a cardiogram waveform display device for displaying cardiogram waveforms comprising: a waveform data storage portion storing waveform data which is converted to digital data from cardiogram waveform signals measured with a cardiograph; a first to an n th filtering means, for carrying out low frequency cut-off processing to the waveform data stored in the storage portion, and for acquiring a first to an n th corrected waveform data, each of the filtering means having a different cut-off frequency; selecting means, for recognizing an amount of variation of a base-line for each segment relative to at least any of the waveform data and the first to the n th corrected waveform data, and for selecting any one of the first to the n th filters in accordance with the amount of variation of the base-line for each of the segments; and display control means for displaying output of the filter selected for each of the segments by the selecting means.

Appropriate corrected waveform data can then be selected and displayed in accordance with the amount of variation of the base-line for each of the segments.

(3) In accordance with characteristics of the present invention, there is provided the cardiogram waveform display device, wherein the display control means simultaneously displays an output of a filter having the lowest cut-off frequency out of the waveform data or the first to the n th corrected waveform data correspondently with an output of a filter selected by the selecting means.

Consequently, the output waveform of the selected filter may compare with that having a lesser base-line restriction.

(4) In accordance with characteristics of the present invention, there is provided the cardiogram waveform display device, wherein the selecting means recognizes an amount of variation of the base-line by calculating feature values of the waveform data or the corrected waveform data at each of the segments.

Hence, it is possible to judge an amount of variation of the base-line in accordance with the feature values.

(5) In accordance with characteristics of the present invention, there is provided the cardiogram waveform display device, wherein the selecting means uses waveform values for at least one of a P-wave, Q-wave, R-wave, S-wave, ST-segment and T-wave, as the feature values.

It is, therefore, possible to use obvious points in the cardiogram waveform at each of the segments as feature values.

(6) In accordance with characteristics of the present invention, there is provided the cardiogram waveform display device, wherein the selecting means uses a waveform value of point Pb or a waveform value of point Qb as the feature value.

Consequently, accurate judgment is possible using one of the waveform value of point Pb and that of point Qb where both become a basic portion of the waveform.

(7) In accordance with characteristics of the present invention, there is provided the cardiogram waveform display device, wherein the larger the difference between the waveform value and a reference value, the selecting means selects a filtering means having a higher cut-off frequency.

Hence, variation of the base-line can be restricted using a filter having a higher cut-off frequency if variation of the base-line in a waveform is large.

(8) In accordance with characteristics of the present invention, there is provided the cardiogram waveform display device, wherein the first cut-off frequency is a low cut frequency for performing functions of a cardiogram monitoring device as defined in the JIST 1304 standard.

It is, therefore, possible to display a waveform as a result of meeting the requirements of a cardiogram monitoring device even if the variation of the base-line is not so large.

(9) In accordance with characteristics of the present invention, there is provided the cardiogram waveform display device, wherein the first filtering means has a first cut-off frequency and the second filtering means has a higher cut-off frequency than the first cut-off frequency, and wherein the selecting means selects one of the first filtering means and the second filtering means.

Consequently, an appropriate filter can be selected from the two filters in response to feature values of the waveform.

(10) In accordance with characteristics of the present invention, there is provided a cardiogram waveform display object for displaying a cardiogram waveform, wherein any one of a first to an n th waveform, out of cardiogram waveforms measured with a cardiograph processed by a first to an n th low frequency cut-off filters, each having a first to an n th cut-off frequency, is selectively displayed in a continuous manner, and wherein the first to the n th waveforms are displayed so that any of the first to the n th waveforms can be displayed, or to which group the waveforms belong, in the case where the first to the n th waveforms are divided into a plurality of groups is displayed.

Hence, the waveform can be displayed even when there is a large variation of the base-line.

(11) In accordance with characteristics of the present invention, there is provided the cardiogram waveform display device, wherein the cut-off frequency of the first to n th filters grows sequentially from the first filter, the second filter, and so on, to the n th filter, and wherein the selecting means calculates an average of absolute values in difference between the first to the n th corrected waveform data for each of the plurality of segments as the feature value, and selects one of the filters in accordance with the averaged value.

It is, therefore, possible to satisfy both restriction of variation of the base-line at the display and display accuracy because any one of the filters are selected for each segment using an average of the absolute values between the first to the n th filters as a criterion for the selection.

(12) In accordance with characteristics of the present invention, there is provided the cardiogram waveform display device and the cardiogram waveform processing program according to characteristic 11 above, wherein the display control means displays either an output of a filter having the lowest cut-off frequency out of the waveform data or the first to the n th corrected waveform data correspondently with an output of a filter selected by the selecting means simultaneously.

Consequently, an output waveform from the selected filter can be compared with that having a small in variation of the base-line.

(13) In accordance with characteristics of the present invention, there is provided the cardiogram waveform display device, wherein the selecting means calculates average values of a first to an n−1 th for each of the segments of the absolute values in difference between the first to the n−1 th corrected waveform data for each of the plurality of segments, and selects a filter having the lowest cut-off frequency among values having equal or less than a predetermined reference value in the average values of the first to the n−1 th.

Hence, both restriction of variation of the base-line at the display and display accuracy are satisfied because any one of the filters is selected for each segment using the absolute values in difference of the output of n th filter, which has a high cut-off frequency, as a criterion for the selection.

(14) In accordance with characteristics of the present invention, there is provided the cardiogram waveform display device, wherein the selecting means selects the n th filter when there is no value equal to or less than the predetermined reference value in the average values of the first to the n−1 th.

It is, therefore, possible to restrict variation of the base-line as much as possible by selecting the n th filter that has the highest cut-off frequency if no appropriate filter is found.

(15) In accordance with characteristics of the present invention, there is provided the cardiogram waveform display device, wherein the selecting means carries out selection of a filter using the averaged difference values together with waveform values for at least one of the P-wave, the Q-wave, the R-wave, the S-wave, the ST-segment and the T-wave as a criterion of the selection.

Consequently, a more appropriate filter can be selected.

(16) In accordance with characteristics of the present invention, there is provided the cardiogram waveform display device and a cardiogram waveform processing program, wherein the first to the fourth filters are provided, each having the first to the fourth cut-off frequency.

Hence, an appropriate filter can be selected from four different ranges of filters in terms of cut-off frequencies.

(17) In accordance with characteristics of the present invention, there is provided the cardiogram waveform display device, wherein the first cut-off frequency is a low cut frequency required by a cardiograph defined in the JIST 1202 standard, and wherein the second cut-off frequency is a low cut frequency required by a cardiogram monitoring device defined in the JIST 1304 standard.

It is, therefore, possible to ensure both accuracy of a cardiograph and that of a cardiogram monitoring device when a variation of the base-line is relatively small.

(18) In accordance with characteristics of the present invention, there is provided the cardiogram waveform display device, wherein the display control means controls such that the first corrected waveform data processed with the first cut-off frequency, the second corrected waveform data processed with the second cut-off frequency, the third corrected waveform data processed with the third cut-off frequency and the fourth corrected waveform data processed with the fourth cut-off frequency are displayed distrainable relative to one another.

Consequently, a judgment can be easily carried out as to whether or not the displayed waveform assures certain accuracy for the cardiograph and the cardiogram monitoring device.

(19) In accordance with characteristics of the present invention, there is provided the cardiogram waveform display device further comprising a fifth to a seventh filter, each having a fifth to a seventh cut-off frequency, respectively.

Hence, an appropriate filter can be selected from seven different ranges of filters in cut-off frequencies.

(20) In accordance with characteristics of the present invention, there is provided the cardiogram waveform display device, wherein the display control means displays a display object so that the display object belonging to, either: any one of the first corrected waveform data through the n th corrected waveform data, or any group of the first corrected waveform data through the n th corrected waveform data being grouped, is identifiably displayed corresponding to the displayed waveform.

It is, therefore, possible to easily recognize which filter is being used.

(21) In accordance with characteristics of the present invention, there is provided the cardiogram waveform display device, wherein the display control means displays a bar, for recognizing whether or not the displayed waveform is corrected waveform data excessively restricting its base-line over a range defined in a corresponding JIS standard, in a vicinity of the display waveform for each segment thereof.

Consequently, judgment whether or not the displayed waveform is an excessively restricted waveform can be easily carried out.

(22) In accordance with characteristics of the present invention, there is provided the cardiogram waveform display device, further comprising feature value calculation means for supplemental use of diagnosing clinical conditions which calculates feature values for supplemental use of diagnosing clinical conditions for one of waveform data and corrected waveform data in each of a plurality of segments, wherein the display control means controls to display the feature values for the supplemental use of diagnosing clinical conditions.

Hence, diagnosis can be carried out easily by displaying not only a cardiogram waveform, but also feature values.

(23) In accordance with characteristics of the present invention, there is provided the cardiogram waveform display device, wherein the display control means displays feature values for supplemental use of diagnosing clinical conditions in accordance with corrected waveform data processed by the filter selected with the selecting means and further controls to carry out displaying thereof for recognizing whether or not the feature values for supplemental use are based on corrected waveform data excessively restricting its base-line over a range defined in a corresponding JIS standard.

(24) In accordance with characteristics of the present invention, there is provided the cardiogram waveform display device, wherein each of the segments represents one cardiac beat.

It is, therefore, possible to display appropriate waveform data for one cardiac beat.

(25) In accordance with characteristics of the present invention, there is provided the cardiogram waveform display device, wherein the display control means adjusts corrected waveform data so that the corrected waveform data is displayed sequentially in accordance with tail waveform data behind the tail of a T-wave of precedent corrected waveform data and corresponding tail waveform data of subsequent corrected waveform data in precedent cardiogram segments, when the continuity of the corrected waveform data to be displayed is lost because the precedent corrected waveform data selected for precedent cardiogram segments and subsequent corrected waveform data selected for subsequent cardiogram segments to the precedent waveform data are different from each other.

Consequently, a smooth waveform display can be carried out even when filters are switched.

(26) In accordance with characteristics of the present invention, there is provided the cardiogram waveform display device, wherein the cardiogram waveform display device either displays which one of a plurality of filters is selected corresponding to an output waveform for each one of a plurality of cardiac beats, or which one of a plurality of filters belonging to which group, to be grouped in a plurality groups, is selected, together with an output waveform of the selected filter for each cardiac beat.

Hence, it is easily ascertainable which displayed waveform was processed by which filter or which filter belongs to which group.

(27) In accordance with characteristics of the present invention, there is provided a method of displaying cardiogram waveforms using a computer comprising the steps of; generating waveform data by converting cardiogram waveform signals measured with a cardiograph to digital data; carrying out low frequency cut-off processing at a first to an n th cut-off frequencies to the waveform data and performing a first to an n th filtering processing for acquiring a first to an n th corrected waveform data; recognizing feature values representing variation of a base-line for each of predetermined segments as to any one of the waveform data and the first to the n th corrected waveform data; and selecting one of the first to the n th filters in accordance with the feature values and displaying output of the filter selected by the selecting means for each of the predetermined segments.

It is, therefore, possible to select an appropriate waveform in accordance with an amount of variation of the base-line for each of the segments and display the selected waveform.

Other features, objects usage and advantages of the present invention will be more apparent to those skilled in the art in consideration of the accompanying drawings.

BRIEF DESCRIPTION OF THE DRAWINGS

FIGS. 8A and 8B are schematic diagrams of describing judgment processing whether or not adopting excessive base-line variation restriction data which is carried out by the CPU of the electrocardiogram monitoring device;

FIG. 19A and FIG. 19B are examples showing variation for displays output through execution of the electrocardiogram display processing;

FIG. 24 is a table showing an example of waveform data and recognition data recorded on a memory 19;

FIG. 25 is a table showing an example of corrected waveform data recorded on the memory 19;

FIGS. 32A, 32B and 32C are graphs showing original waveforms and base-line variation restricting waveforms according to the fourth embodiment; and FIGS. 33A, 33B and 33C are graphs showing original waveforms and base-line variation restricting waveforms according to the fourth embodiment.

DESCRIPTION OF REFERENCE NUMERALS

Figure 1:
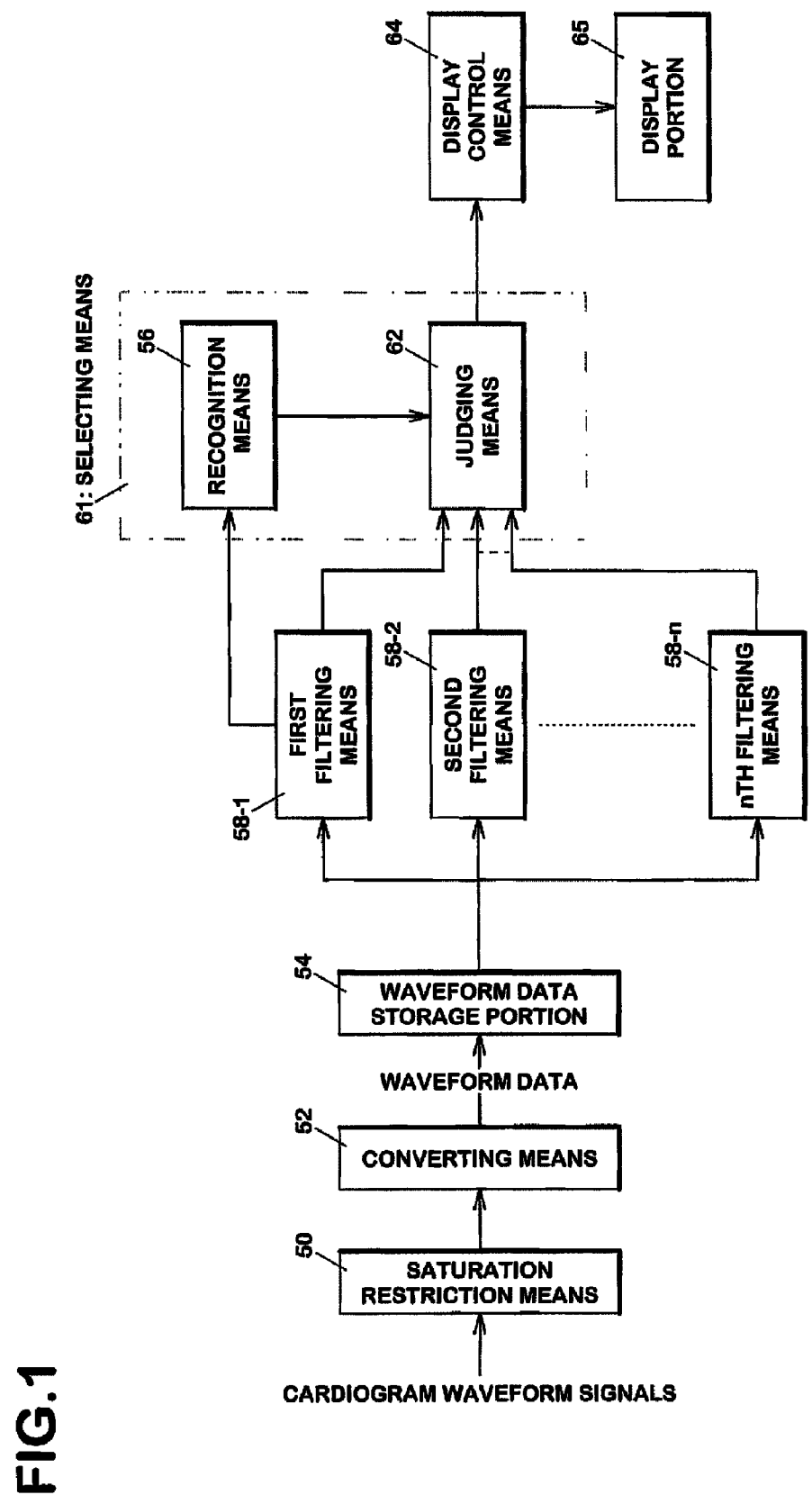
FIG. 1 is a functional block diagram of an electrocardiogram monitoring device according to an embodiment of the present invention.

100 . . . Cardiogram monitoring device
22 . . . ECG electrodes
12 . . . ECG input circuitry
17 . . . Base-line variation restricting filter
18 . . . Excessive base-line variation restricting filter

DETAILED DESCRIPTION OF THE PREFERRED EMBODIMENTS

An electrocardiogram monitoring device 100 corresponding to one of "electrocardiogram waveform display device" and "a method of displaying electrocardiogram waveform" according to the present invention is a device for displaying and/or printing electrocardiograms of a patient.
Table of Contents
1. Outline of the electrocardiogram display device
2. Device structure
3. Description of device functions
4. First embodiment
5. Second embodiment
6. Advantages of the embodiments
7. Third embodiment
8. Fourth embodiments
9. Other embodiments

1. Outline of the Electrocardiogram Display Device

Figure 3:
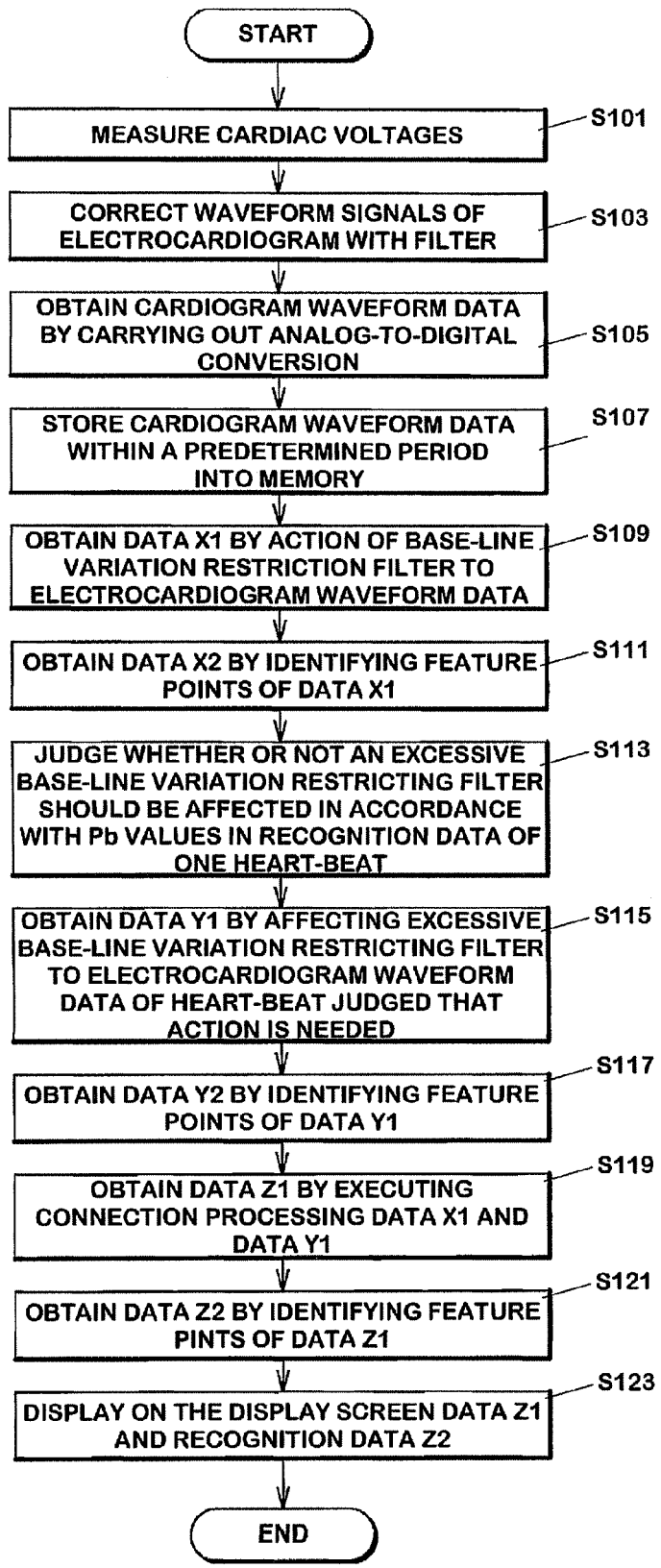
FIG. 3 is a flowchart outlining electrocardiogram display processing according to an exemplary embodiment.

FIG. 3 is a flowchart (flowchart of electrocardiogram waveform display processing program) outlining electrocardiogram processing carried out by the electrocardiogram monitoring device 100 according to an embodiment of the present invention. This electrocardiogram display processing is for displaying electrocardiograms by restricting a variation of a base-line of electrocardiogram waveforms. By carrying out such restriction, a user of the device can easily recognize variations of an ST level (one of the components of electrocardiogram waveform) and supplementary diagnosis of cardiac disease can also be easily done. The monitoring device 100 may also be used in a location where first-aid is needed, in an ambulance, in a hospital, or in any place where electrocardiogram analysis is carried out.

The monitoring device 100 measures cardiac voltages (step S101) and corrects the waveform signals of the electrocardiogram with a filter (S103). Then the monitoring device 100 obtains electrocardiogram waveform data by carrying out analog-to-digital conversion of the corrected waveform signals (S105). The monitoring device 100 stores the cardiogram waveform data within a predetermined period (from the start of electrocardiogram measurement to the end thereof) into a memory (S107).

The monitoring device 100 obtains base-line variation restriction data X1 through the action of a base-line variation restriction filter that will be described later in relation to the electrocardiogram waveform data (S109). The monitoring device 100 obtains base-line variation restriction data X2 by identifying feature points of the waveforms indicated by the data X1 (S111). Such feature points are based upon one of the components of the electrocardiogram waveform such as a P wave, Q wave, R wave, S wave, ST-segment and T wave.

The monitoring device 100 judges whether or not an excessive base-line variation restricting filter should be applied to the electrocardiogram waveform data in accordance with Pb values (values related to the P wave) contained in recognized data of one heart-beat (S113). Then the monitoring device 100 obtains excessive base-line variation restriction data Y1 by applying the excessive base-line variation restricting filter to the electrocardiogram waveform data of the heart-beat being judged as needing excessive base-line variation restricting filtering (S115). The monitoring device 100 further obtains recognition data Y2 by identifying feature points of waveforms represented by the excessive base-line variation restriction data Y1 (S117).

The monitoring device 100 obtains waveform connection data Z1 by executing connection processing so that a base-line variation restriction waveform according to the base-line variation restriction data X1 and the excessive base-line variation restriction waveform according to the excessive base-line variation restriction data Y1 are sequentially displayed (S119). The monitoring device 100 further obtains recognition data Z2 by identifying feature points of waveforms represented by the waveform connection data Z1 (S121). The monitoring device 100 then displays on the display screen a connected waveform based on the waveform connection data Z1 and the recognition data Z2 (S123), thereafter with the process ending.

Figure 16:
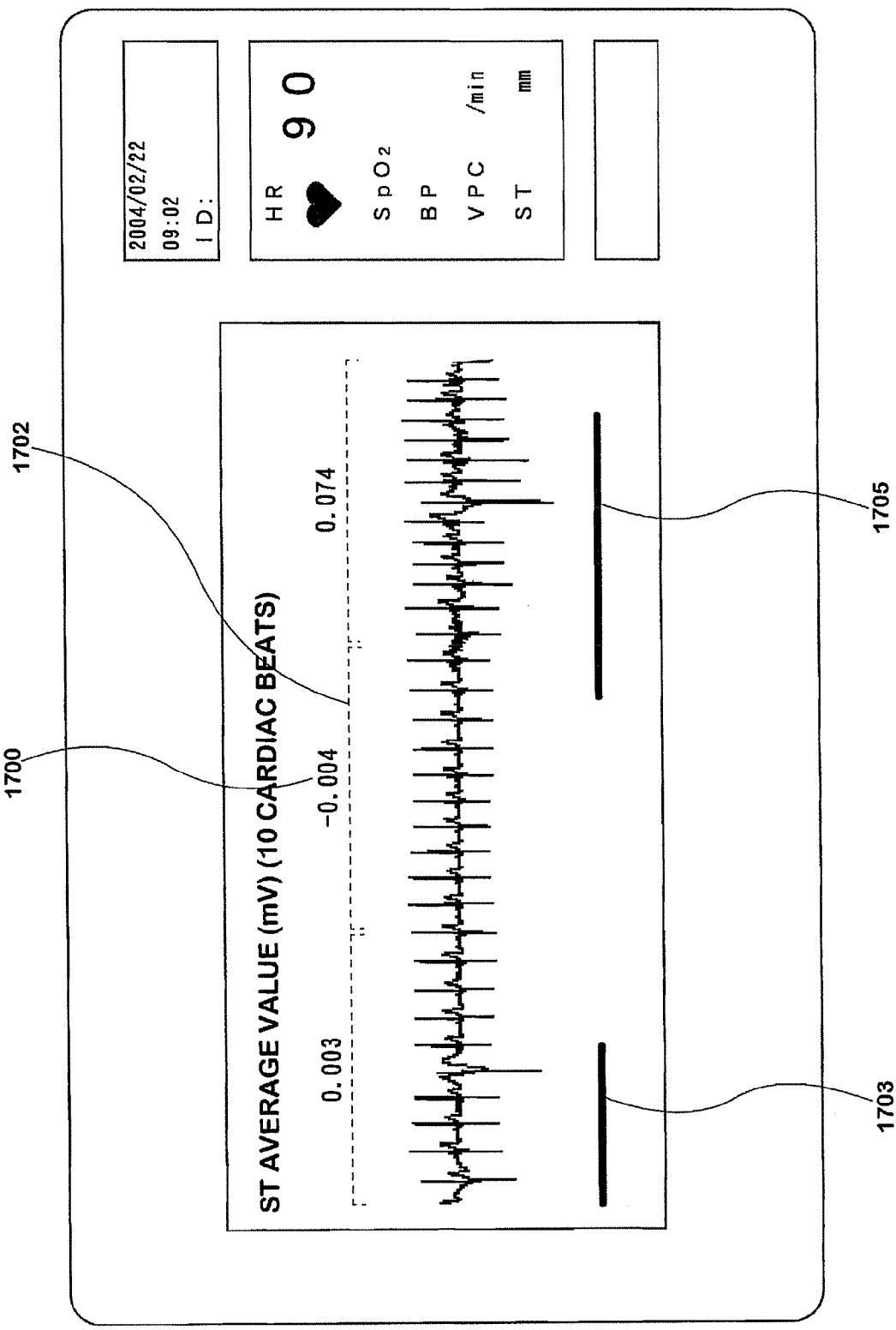
FIG. 16 is display examples output through execution of the cardiogram display processing.

FIG. 16 shows an example of a display where the monitoring device 100 displays both the base-line variation restriction waveform and the excessive base-line variation restriction waveform. In particular, both identification marks 1703 and 1705 are displayed together with an electrocardiogram (ECG) waveform which becomes the excessive base-line variation restriction waveform.

2. Device Structure 2-1. Functional Block

FIG. 1 shows a functional block of the electrocardiogram monitoring device 100. Electrocardiogram waveform signals are provided to converting means 52 via saturation restriction means 50. The converting means 52 converts the electrocardiogram waveform signals which are analog signals into digital waveform data. The saturation restriction means 50 prevents saturation of the converting means 52 when the electrocardiogram waveform signals exceed an allowable input voltage of the converting means 52.

The waveform data generated by the converting means 52 is stored in a waveform data storage portion 54. A first filtering means 58-1 through n th filtering means 58-n are low-cut filters, each having a first cutoff frequency fc1 through an n th cutoff frequency fcn respectively. These filters are constructed so that first cutoff frequency fc1 is the lowest cutoff frequency and frequency grows by the second cutoff frequency fc2, the third cutoff frequency fc3 . . . and so on, to the n th cutoff frequency fcn.

As to the first filtering means 58-1, while influence for waveforms is the smallest, such first filtering means is easy to be affected by a variation of the base-line. In contrast, while influence for waveforms of the n th filtering means 58-n is the largest, such n th filtering means is hardly affected by variation of the base-line.

Recognition means 56 recognizes feature values of waveforms related to a variation of the waveforms in accordance with any outputs (or two or more outputs) of the first filtering means 58-1 through the n th filtering means 58-n. Judging means 62 selects which of the first through the n th filter is used based on the recognized feature values with the recognition means 56. A filter which restricts base-line variation is used when the base-line variation is large, and a filter having less influence on waveforms is used when the base-line variation is small. In this embodiment, selecting means 61 comprises the recognition means 56 and the judging means 62.

Display control means 64 displays on a display portion 65 output of the selected filter.

Figure 2:
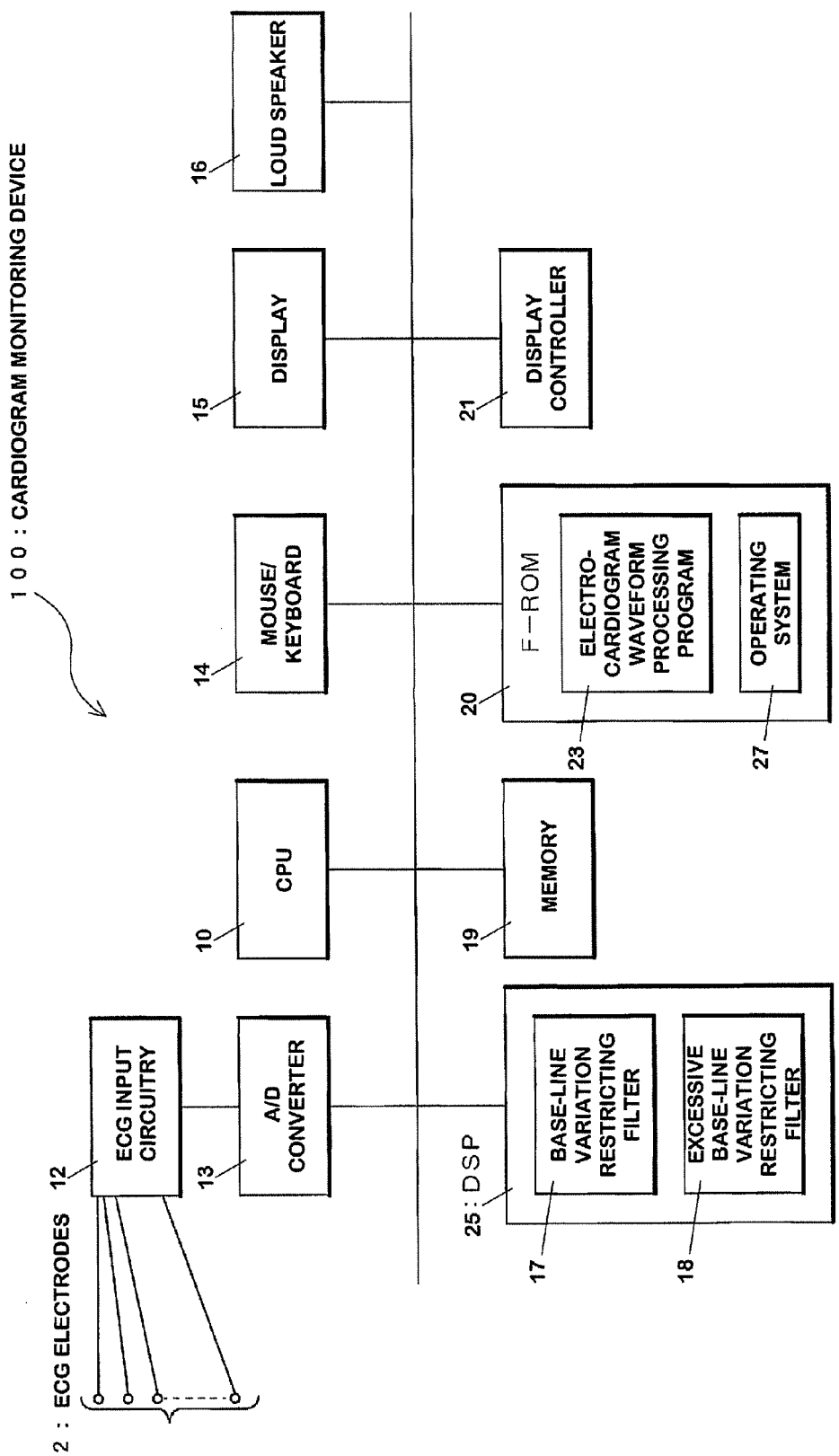
FIG. 2 is an example of hardware structure of the electrocardiogram monitoring device.

FIG. 2 shows an exemplary hardware structure realizing the electrocardiogram monitoring device 100 shown in FIG. 1 using a CPU. The monitoring device 100 comprises a CPU 10, ECG electrodes 22 (biological signal detectors), an ECG input circuitry 12, an A/D (analog/digital) converter 13, a mouse/keyboard 14, a display 15 (display device), a loud speaker 16, a DSP 25 (a base-line variation restricting filter 17, an excessive base-line variation restricting filter 18), a memory 19, a Flash-ROM 20 (a memory capable of electrically erasing/updating recorded data such as a flash memory, hereinafter referred to as FROM 20, that can be substituted for a hard disk) and a display controller 21.

The ECG electrodes 22 are electrodes for measuring cardiac voltages of a patient. The CPU 10 controls overall operation of the monitoring device 100 in addition to performing electrocardiogram display processing in accordance with cardiac voltage signals thus obtained. The F-ROM 20 stores both an electrocardiogram waveform processing program 23 which is used by the monitoring device 100 and an operating system 27. The memory 19 (or the F-ROM20) is used as a work region of the CPU 10 and a storage region for obtained data. The display controller 21 is used for controlling a display screen of the display 15, and so on. The function of the ECG input circuitry 12, of the base-line variation restricting filter 17 and of the excessive base-line variation restricting filter 18 will be described later.

In the embodiments, an example of the operating system (OS) 27 used for the monitoring device 100 is one of Microsoft Windows (Registered Trademark) XP, NT, 2000, 98SE, ME, CE, and so on. Although, the processing program 23 used in this embodiment cooperates with the OS in order to achieve each of the functions shown in FIG. 1, these functions may also be achieved by the processing program 23 itself.

The term "Cardiogram" described in the embodiments is obtained by measuring a difference in electric potentials for two points of the body of an examinee. It is, therefore, the term "measurement of cardiogram" includes a concept of measuring electric potentials of the heart.

In an embodiment described below, a case where both the first filter and the second filter are provided (that is, n=2) will be described.

2-2. ECG Input Circuitry

Figure 4:
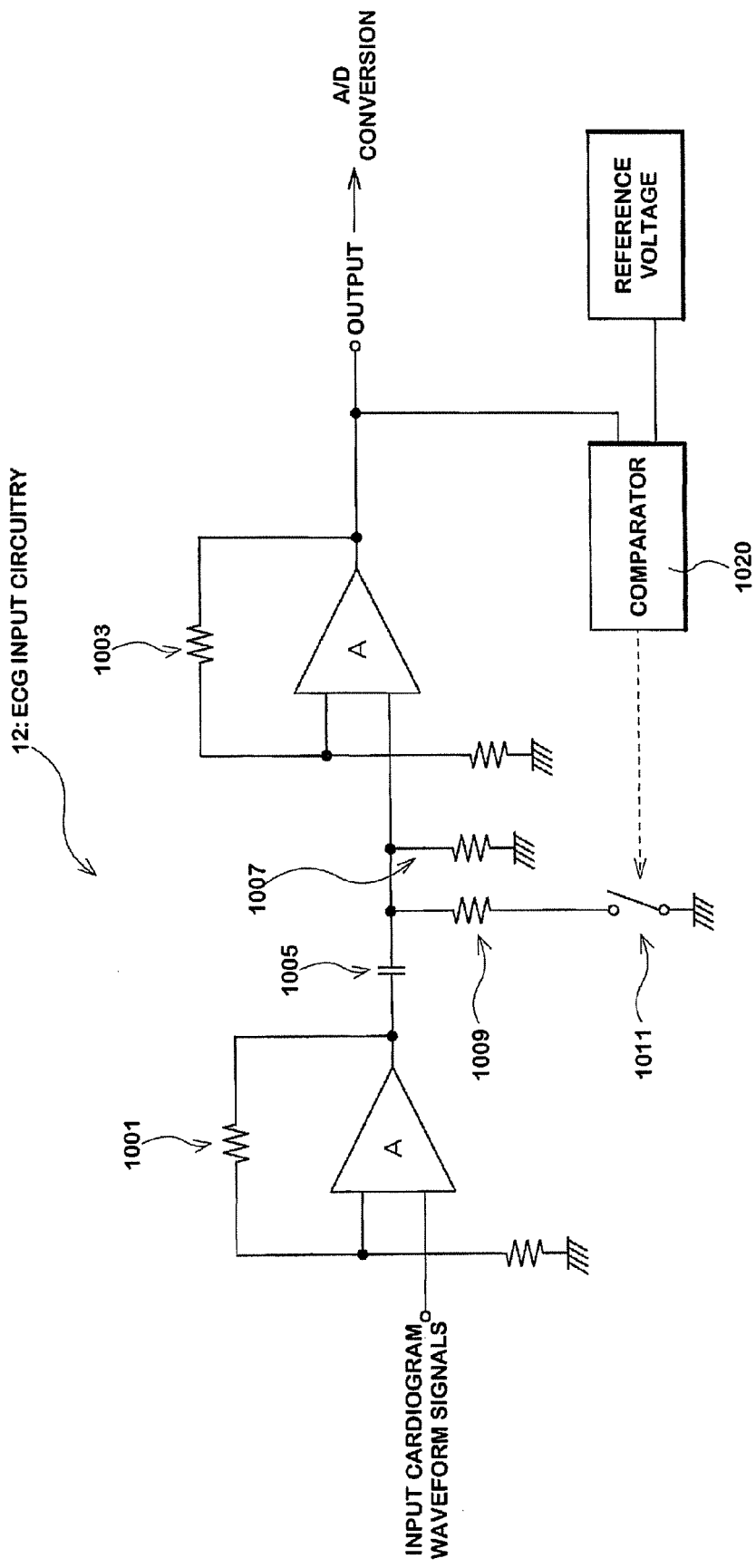
FIG. 4 is a block diagram of an ECG input circuitry included in the electrocardiogram monitoring device.

FIG. 4 is a block diagram illustrating an embodiment of the ECG input circuitry 12 shown in FIG. 2. The ECG input circuitry 12 is well-known to the person skilled in the art as a reset circuitry. The input circuitry 12 comprises an operational amplifier 1001, another operational amplifier 1003, a capacitor 1005, a resistor 1009, another resistor 1007, a switch 1011, and so on. In particular, the input circuitry amplifies cardiac voltage signals (cardiac current signals) input through the ECG electrodes 22 to predetermined times and outputs them to the A/D converter 13. The degree of restriction is depending upon the capacitor 1005 and the resistor 1007. In this way, cardiac current signals are adjusted within a voltage range (dynamic range) that can be handled by the A/D converter 13.

Further, when the cardiac voltage signals vary more than a reference voltage (for example, an excessive electrical potential variation occurs by using a cardiac defibrillator on an examinee), the comparator 1020 detects it. The switch closes when the comparator 1020 detects such a condition. Consequently, the degree of restriction becomes higher and this can prevent saturation of the A/D converter 13.

2-3. Base-line Variation Restricting Filter (First Filter)

Figure 5:
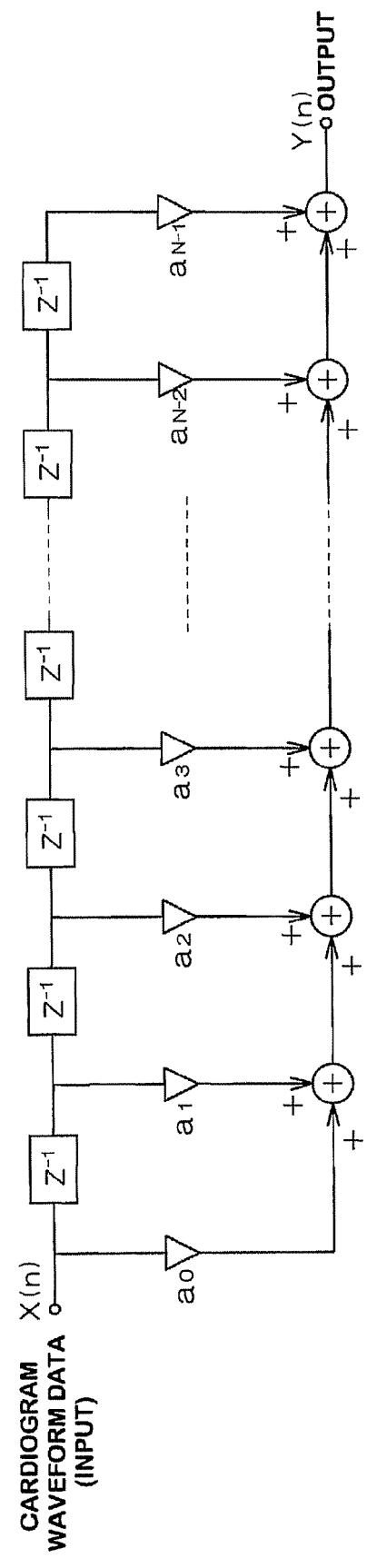
FIG. 5 is a signal flow diagram of a base-line variation restricting filter included in the electrocardiogram monitoring device.

In this embodiment, the base-line variation restricting filter 17 is realized by the DSP 25. FIG. 5 shows a signal flow diagram of the base-line variation restricting filter 17. The base-line variation restricting filter 17 may be constructed by hardware logic (hardware logic circuitry).

The CPU 10 provides the waveform data recorded on the memory 19 to the base-line variation restricting filter 17. The base-line variation restricting filter 17 makes the filtered first corrected waveform data to be recorded on the memory 19.

Such base-line variation restricting filter 17 is a low cut-off filter, and examples of its fundamental characteristics are as follows.

Sampling frequency: 250 Hz
Signal pass frequency range: equal to or more than 0.7 Hz (±5%)
Cutoff frequency: 0.5 Hz (−3 dB)
Signal delay period: 1200 msec. (millisecond)

The base-line variation restricting filter 17 shown in FIG. 5 can be a FIR filter, and the above-mentioned fundamental characteristics are realized by comprising approximately 500 to 1000 steps of multipliers, adders and unit delay elements in this embodiment. The base-line variation restricting filter 17 may adopt other structures, and a device capable of realizing the above-mentioned fundamental characteristics is not limited to the structure shown in FIG. 5.

2-4. Excessive base-Line Variation Restricting Filter (Second Filter)

Figure 6:
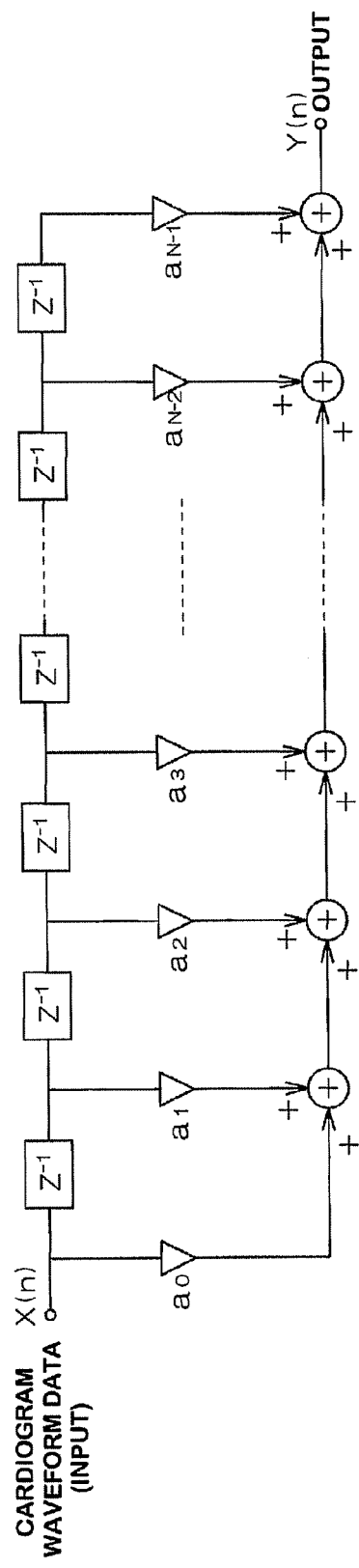
FIG. 6 is a signal flow diagram of an excessive base-line variation restricting filter included in the electrocardiogram monitoring device.

In this embodiment, the excessive base-line variation restricting filter 18 is realized by the DSP 25. FIG. 6 shows a signal flow diagram of the excessive base-line variation restricting filter 18. The base-line variation restricting filter 18 may be constructed by hardware logic (hardware logic circuitry).

The CPU 10 provides the waveform data recorded on the memory 19 to the excessive base-line variation restricting filter 18. The excessive base-line variation restricting filter 18 records the filtered second corrected waveform data on the memory 19.

Such excessive base-line variation restricting filter 18 is a low cut filter, and examples of its fundamental characteristics are as follows.

Sampling frequency: 250 Hz

Signal pass frequency range: equal to or more than 2 Hz (±5%)

Cutoff frequency: 1.45 Hz (−3 dB)

Signal delay period: 400 msec. (millisecond)

The excessive base-line variation restricting filter 18 shown in FIG. 6 can be a FIR filter, and the above-mentioned fundamental characteristics are realized by comprising approximately 500 to 1000 steps of multipliers, adders and unit delay elements in this embodiment. In the embodiments, the above-mentioned fundamental characteristics of the excessive base-line variation restricting filter 18 are realized by changing the factor (variable) of each component and/or the number of steps in the base-line variation restricting filter 17. The excessive base-line variation restricting filter 18 may adopt other structures, and a device capable of realizing the above-mentioned fundamental characteristics is not limited to the structure shown in FIG. 6.

3. Description of Device Functions

Correspondence between each component of the electrocardiogram monitoring device 100 shown in FIG. 1 and each function of the embodiments are as follows.

Saturation restricting means 50 corresponds to the ECG input circuitry 12. The converting means 52 corresponds to A/D converter 13. Also, the waveform data storage portion 54 corresponds to the memory 19. Further, first filtering means 58-1 corresponds to the base-line variation restricting filter 17 in the first and the second embodiment or the base-line variation restricting filter 17a in the third and the fourth embodiments. Still further, second filtering means 58-2 corresponds to the excessive base-line variation restricting filter 18 in the first and the second embodiments or a base-line variation restricting filter 17b in the third and the fourth embodiments. Third through seventh filtering means 58-3 to 58-7 respectively correspond to the base-line variation restricting filters 17c to 17g in the third and the fourth embodiments.

Figure 12:
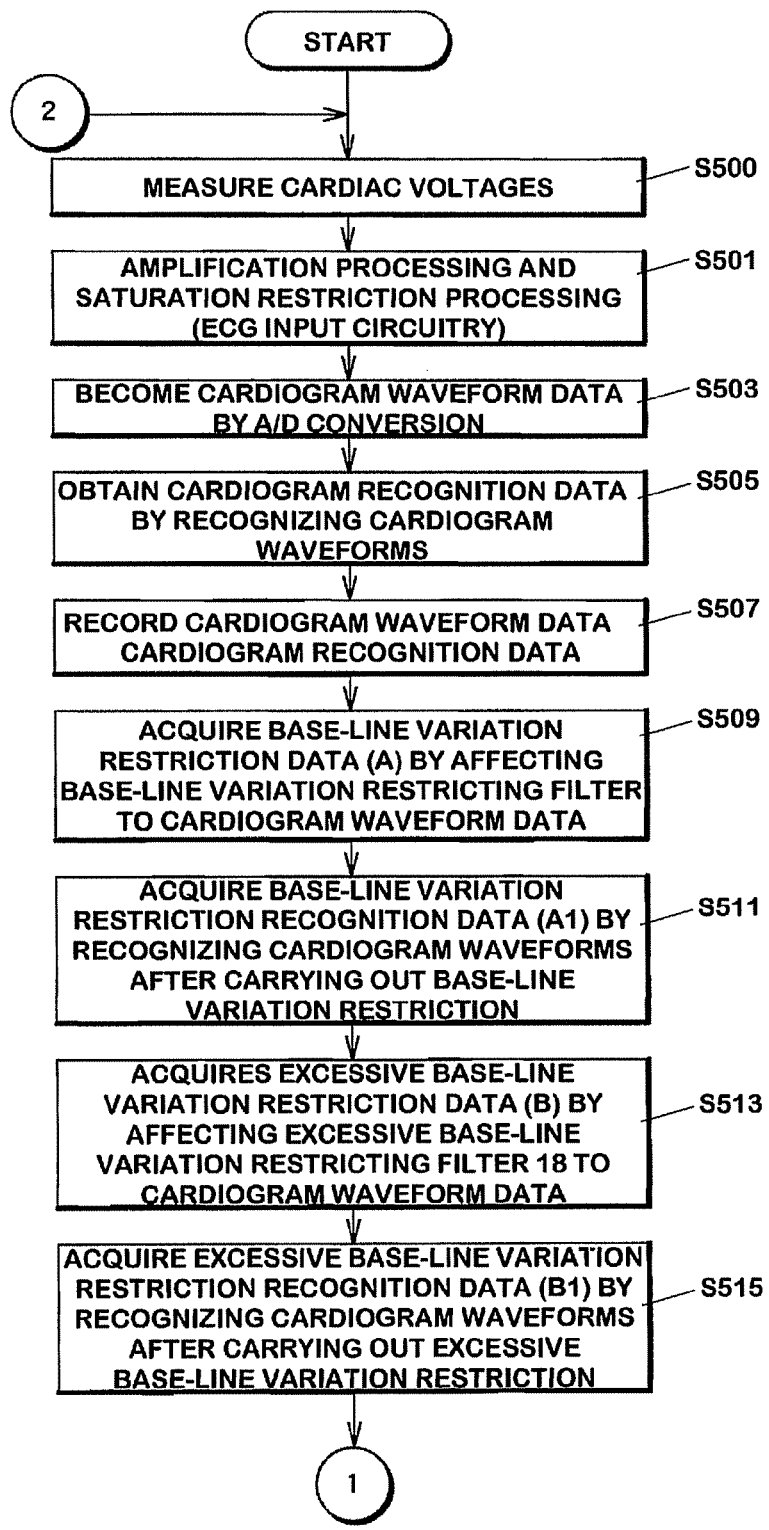
FIG. 12 is a flowchart of an electrocardiogram display processing program according to a first embodiment.
Figure 13:
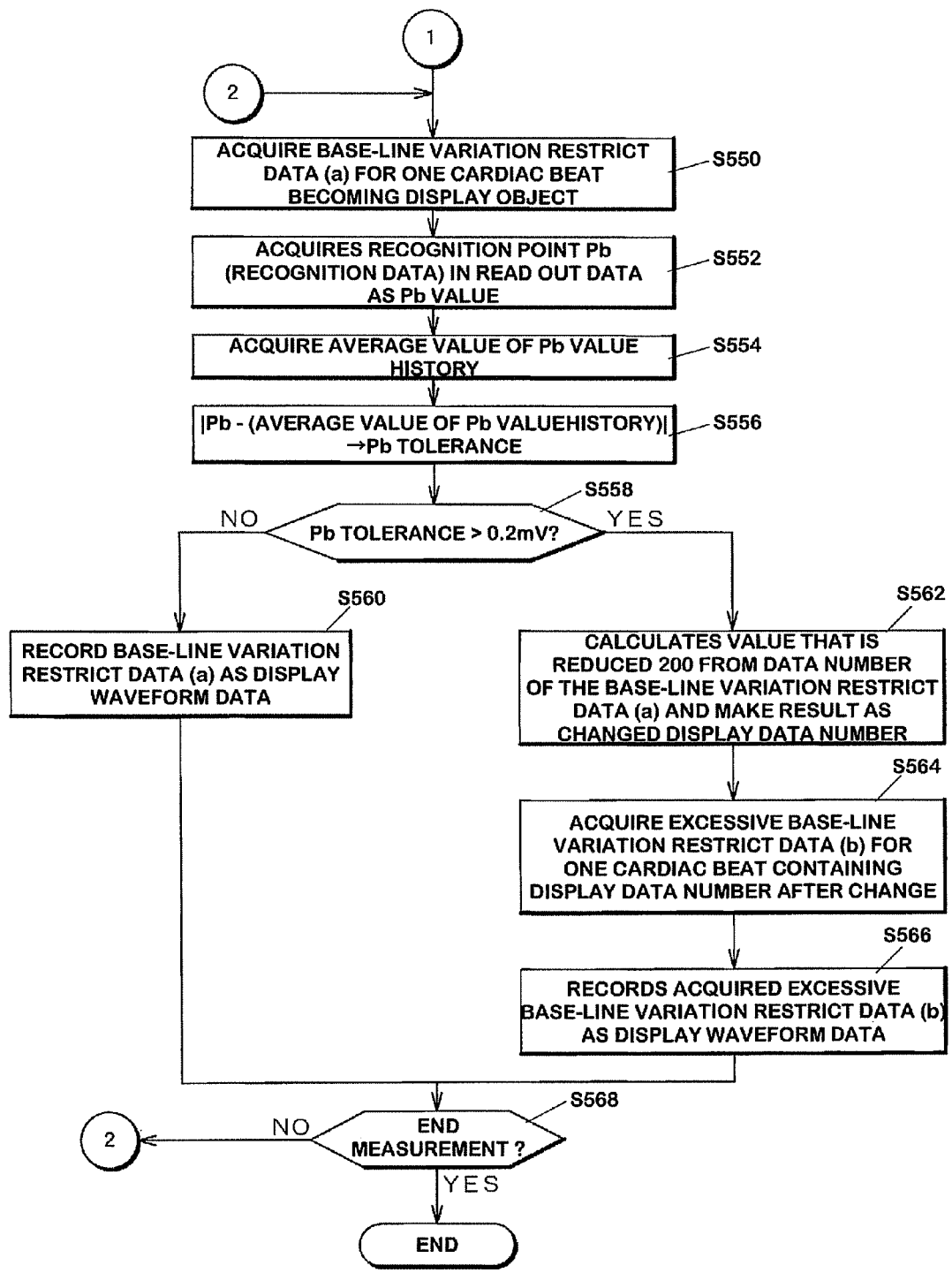
FIG. 13 is another flowchart of the electrocardiogram display processing program according to the first embodiment.
Figure 23:
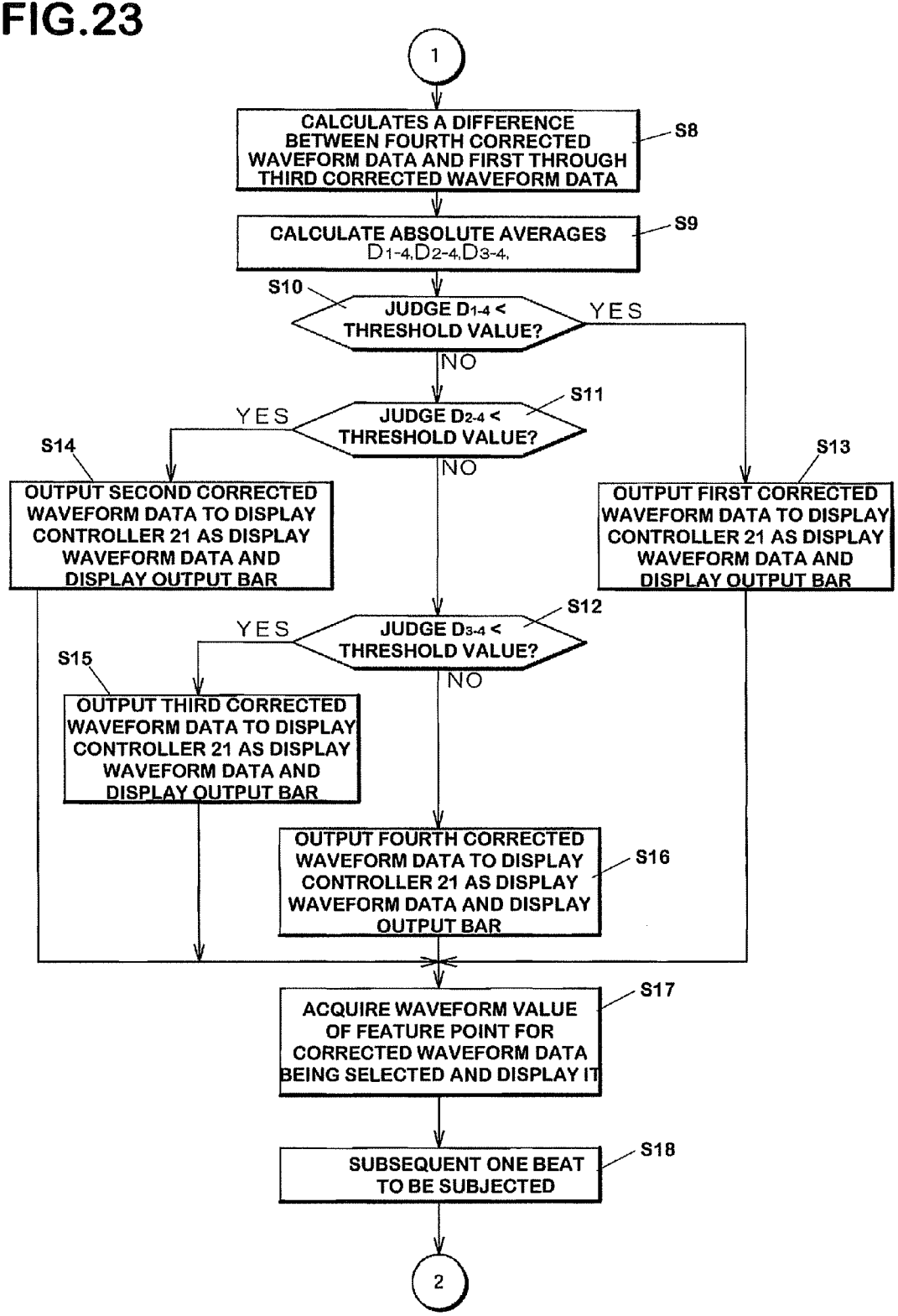
FIG. 23 is another flowchart of the electrocardiogram display processing program according to the third embodiment.
Figure 26A:
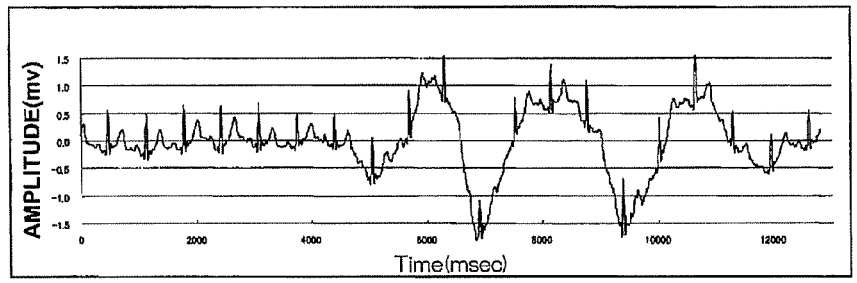
FIGS. 26A, 26B, 26C and 26D are graphs for showing the first to fourth corrected waveform data processed with the base-line variation restricting filters 17a through 17d.
Figure 26B:
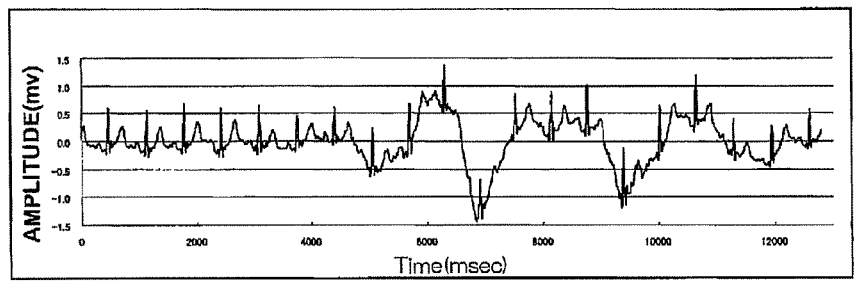
Figure 26C:
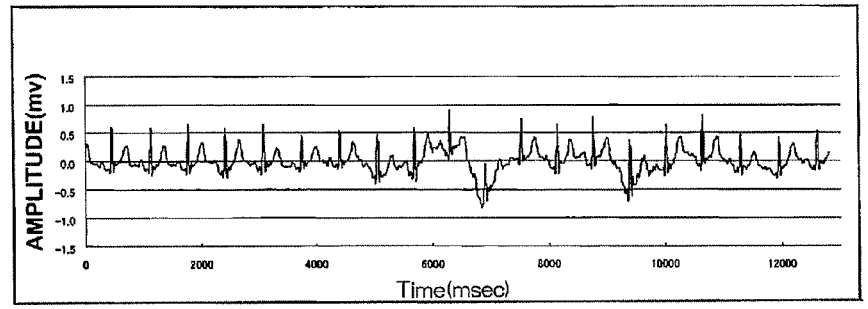
Figure 26D:
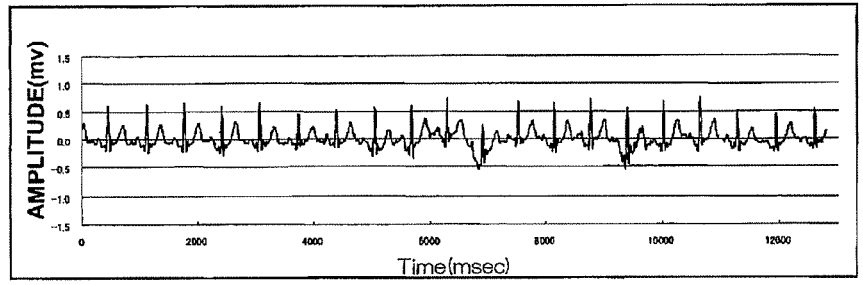

The recognition means 56 corresponds to the CPU 10 performing step S511 of FIG. 12 and steps S8 and S9 of FIG. 23. Also, the judging means 62 corresponds to the CPU 10 executing steps S550, 552, 554, 556, 558, 560, 562, 564 or 566 in FIG. 13 or that perform steps S10 to S12 as shown in FIG. 23. Further, the display control means 64 corresponds to the CPU 10 carrying out steps S560, S566 as shown in FIG. 13 or that perform steps S13 through S16 in FIG. 23. Moreover, the display portion 65 corresponds to the display 15.

In this invention, the filtering means executing low frequency cut-off processing is a concept including in both the cases in which such processing is carried out with either software or hardware. Also, the filtering means performing the low frequency cut-off processing represents filtering means carrying out at least low frequency cut-off processing, and it contains the one cut-off of a particular frequency in addition to cut-off of low frequencies.

4. First Embodiment

4.1. Flowchart of Cardiogram Waveform Processing

Flowcharts of the waveform processing program 23 executed by the CPU 10 of the monitoring device 100 will be described with reference to the drawings. FIGS. 12, 13 are flowcharts of the waveform processing program according to the first embodiment.

The CPU 10 of the monitoring device 100 measures cardiac voltages of an examinee via the ECG electrodes 22 (FIG. 12, step S500). The measured voltage signals become cardiogram waveform data upon execution of amplification processing and saturation restriction processing (S501) by the ECG input circuitry 12 and of A/D conversion processing by the A/D converter 13 (S503). Such cardiogram waveform data is recorded on the memory 19.

Subsequently, the CPU 10 reads out the cardiogram waveform data recorded on the memory 19 and recognizes the feature values for cardiogram waveforms represented by the cardiogram waveform data (S505).

Figure 7:
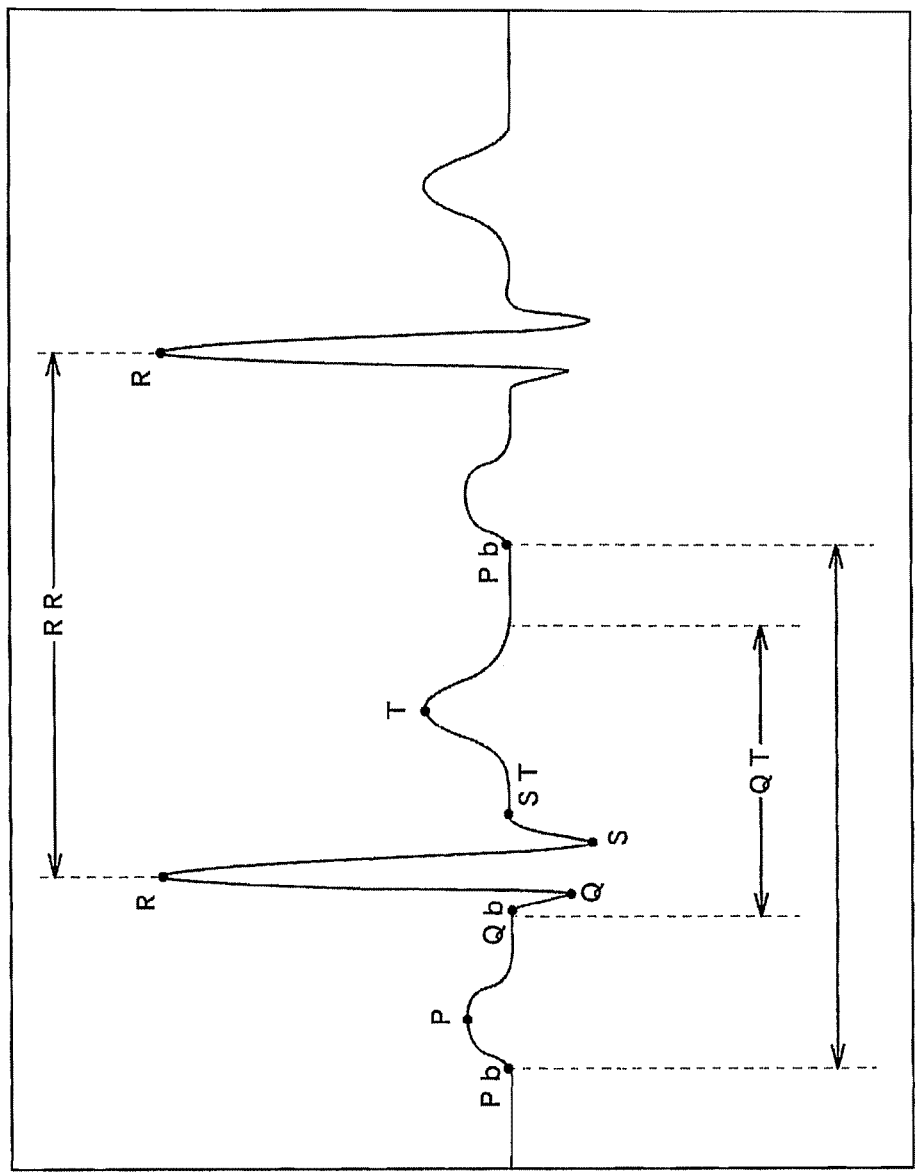
FIG. 7 is a schematic diagram of recognition data acquired by a CPU of the electrocardiogram monitoring device.

In particular, the CPU 10 recognizes waveforms for each cardiac beat in accordance with the cardiogram waveform data. FIG. 7 is a schematic diagram of recognition data obtained by execution of the processing of step S505 with the CPU 10. As shown in FIG. 7, the CPU 10 recognizes one cardiac beat by recognizing (extracting) all or part of P (P-electric potential or P-wave height), Q (Q-electric potential or Q-wave height), R (R-electric potential or R-wave height), S (S-electric potential or S-wave height), T (T-electric potential or T-wave height), ST (ST-level), QT (QT-interval), and RR (RR-interval) from the cardiogram waveform data. The CPU 10 recognizes one cardiac beat and each of the waves in the cardiogram by performing the following process when the waveform is determined to be normal.

(1) Recognition of one cardiac beat: the RR interval is recognized as one heart beat through recognition of an R-wave representing the maximum component over a threshold value and upcoming R-wave (representing the maximum component over the threshold value). At that time, waveforms, from which a T-wave component (less frequency than the R-wave) that is one of the peak values except for the R wave is removed using a low cut filter, are separately generated, and the R-wave may be recognized based on the generated waveforms. Not only the amplitude value of the R-wave, but also its time (or information on sequence) may be recognized (the same as that in the recognitions described below).

(2) Q-wave: The bottom value right before the R-wave is recognized as a Q-wave. Further, waveform values (amplitude) of point Qb are calculated. The point Qb is recognized as the origin of a waveform that extends to the minimum point of the Q-wave. In particular, a differential value of each point is calculated by going back in terms of time from the minimum point of the Q-wave, and a point at which the differential value drastically comes close to 0 is recognized as the point Qb.

(3) P-wave: The peak value that exists at a position prior to 200~300 msec (milliseconds) of the Q-wave is recognized as the maximum point of the P-wave. Further, waveform values (amplitude) of point Pb are calculated. The point Pb is recognized as the origin of a waveform that extends to the maximum point of the P-wave. In particular, a differential value of each point is calculated by going back in terms of time from the maximum point of the P-wave, and a point at which the differential value drastically comes close to 0 is recognized as the point Pb.

(4) S-wave: The bottom value right after the R-wave (a bottom value equal or more than a predetermined threshold value)(less value than that of R-wave) is recognized as an S-wave.

(5) T-wave: The peak value existing between the first R-wave and the second R-wave (a peak value equal or more than a predetermined threshold value) (less value than that of R-wave) is recognized as a T-wave.

(6) ST-segment: The maximum region(s) between the S-wave and the T-wave is recognized as an ST-segment when the S-wave and the T-wave are in linear interpolation. Further, the amplitude value at a position after having passed 60 ms from the ST-segment is recognized as ST60 and that at a position after having passed 80 ms from the ST-segment is recognized as ST80.

As described in the above, the CPU 10 calculates amplitude values and temporal positions of the Q-wave, point Qb, the P-wave, point Pb, the S-wave, the T-wave, the ST-segment, ST60 and ST80 as cardiogram recognition data. The duration from the point Pb and upcoming point Pb is recognized as one cardiac beat.

In a cardiogram measurement, there might be a high possibility for high frequency noises having an abnormal cycle unexpectedly occurring depending on behaviors of the examinee during the measurement and extraction of recognition data, especially if the measurement is not correctly performed. In order to measure accurate recognition data without such high frequency noises, the technique disclosed in Japanese Patent Laid-Open Publication No. Hei06-261871 may be used.

Besides recording cardiogram waveform data of a patient into the memory 19, the CPU 10 carries out the above-described recognition and records cardiogram recognition data into the memory 19 (or other storage device, the same applied below) (S507).

The CPU 10 acquires base-line variation restriction data (for explanation purposes illustrated with symbol (A), the same as that in each of the data shown below) by applying the base-line variation restricting filter 17 to the cardiogram waveform data and records the restriction data into the memory 19 (S509). The CPU 10 then recognizes feature values for cardiogram waveforms represented by the base-line variation restriction data (A) under the same procedure for step S505 and records the recognized data in the memory 19 as base-line variation restriction recognition data (A1) (S511).

The CPU 10 acquires excessive base-line variation restriction data (B) by affecting the excessive base-line variation restricting filter 18 to the cardiogram waveform data and records the restriction data into the memory 19 (S513). The CPU 10 then recognizes feature values for cardiogram waveforms represented by the excessive base-line variation restriction data (B) under the same procedure for step S505 and records the recognized data in the memory 19 as excessive base-line variation restriction recognition data (B1) (S515).

Figure 9:
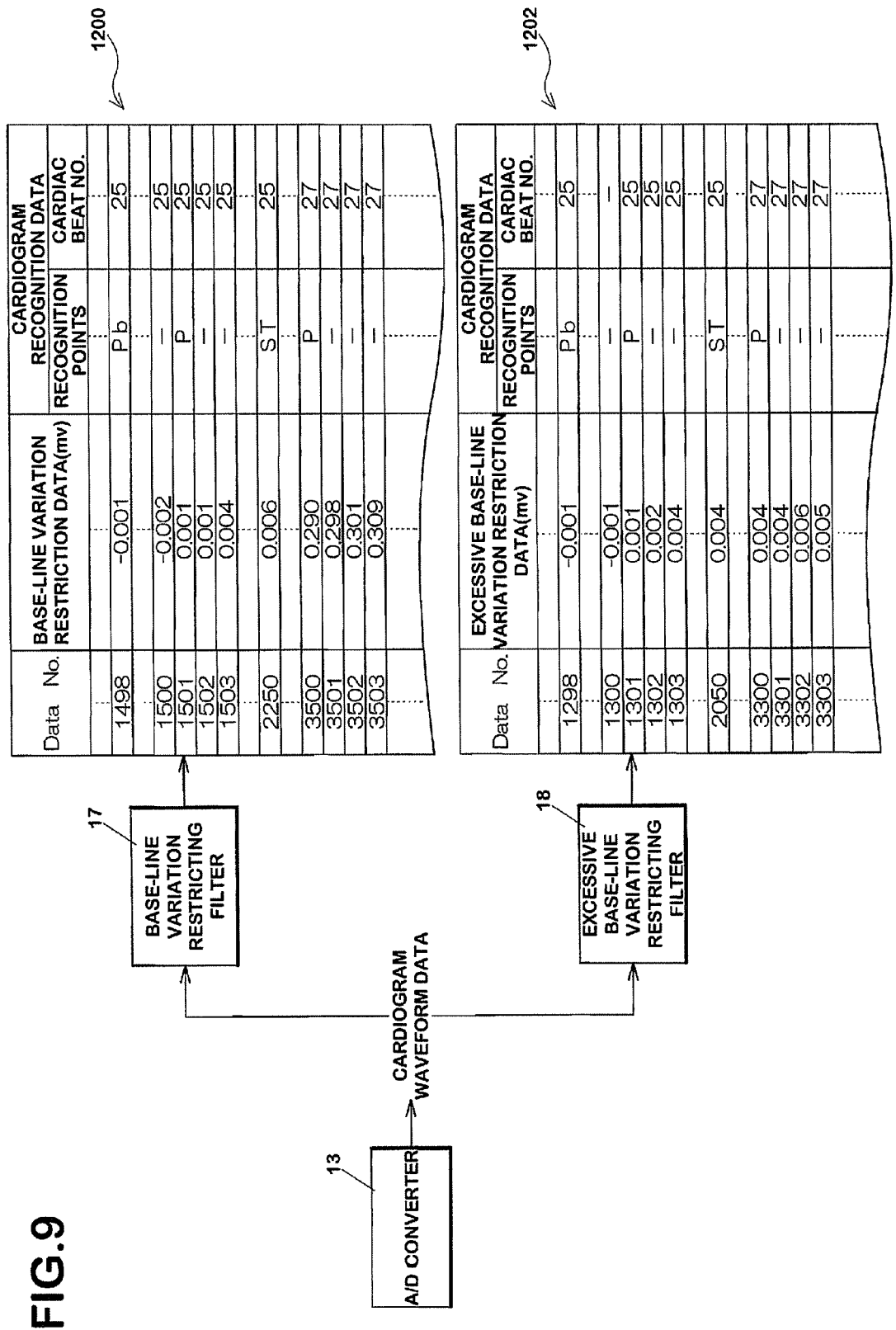
FIG. 9 is a schematic diagram illustrating base-line variation restriction data and excessive base-line variation restriction data.

FIG. 9 is a schematic diagram illustrating the base-line variation restriction data (A) under the procedure for step S511 and the excessive base-line variation restriction data (B) under the procedure for step S515. For example, as shown in the drawing, the CPU 10 records data 1200 into the memory 19 by affecting the base-line variation restricting filter 17 to the cardiogram waveform data after processing of the A/D converter 13 (see S509). Each data contained in the data 1200 is specified by data number. In particular, each data is generated by applying the base-line variation restricting filter 17, such data is recorded correspondently with the data number representing the sequence of generating thereof in the memory 19. Such data number is an embodiment of "information on generation sequence". Information on time, representing a time at which time data is generated, can be used as another embodiment of the "information on generation sequence". One base-line variation restriction data (measurement unit: millivolt (mV)) is generated for every 0.004 seconds of voltage measurement duration because the sampling frequency is 250 Hz in this embodiment. As shown in the drawing, the base-line variation restriction data contained in the data 1200 is recorded so that the restriction data corresponds to base-line variation restriction recognition data obtained through the processing performed at step S511. Such recognition data contains "recognition points" representing components according to any one of point Pb, P-wave, point Qb, Q-wave, R-wave, S-wave, ST-segment, ST60, ST80 and T-wave, and the like, such as cardiogram components and "cardiac beat number" representing the sequence of the recognized cardiac beat. For example, data number "1501" shows information on cardiac voltage "0.001 mV", recognition point "P (corresponding to P-wave)" and cardiac beat number "25". Similarly, the CPU 10 records data 1202 into memory 19 by applying the excessive base-line variation restricting filter 18 to the cardiogram waveform data after processing of the A/D converter 13 (see S513). Content of each data contained in the data 1202 is identical to that of the data 1200.

The CPU 10 determines which of the base-line restriction data or the excessive base-line restriction data is used as an object to be displayed of cardiogram for each cardiac beat, and displays the display object after determination of all the cardiac beats within the measurement period.

The CPU 10 reads out from the memory 19 base-line variation restriction data (a) corresponding to a range of one cardiac beat that becomes the display object (FIG. 13, step S550). Judgment of one cardiac data by the CPU 10 can be performed using information of the cardiac beat number shown in FIG. 9, for example. In the embodiment, the CPU 10 acquires data within a range corresponding to a range from a recognition point P to recognition point T (or data just before an upcoming P).

Then the CPU 10 acquires base-line variation restriction data of the recognition point Pb (a value related to the P-wave) in the read out data as a Pb value (S552). The CPU 10 acquires an average value of the Pb value history (S554). In the embodiment, the CPU 10 calculates an average value of base-line variation restriction data of the past 10 cardiac beats at the recognition point Pb acquired at step S550 and makes the calculated value as a reference value. Further, the CPU 10 calculates an absolute value (Pb tolerance) of a difference between the Pb value acquired at step S552 and an average value (reference value) of the Pb value history acquired at step S554 (S556). The reference value may also be an absolute threshold value instead of this average value.

The CPU 10 judges whether or not the calculated Pb tolerance is above 0.2 mV (S558). By carrying out this processing, it is judged whether or not a large variation of the base-line occurs on waveforms shown by the base-line variation restriction data in comparison with waveforms of the past cardiac beats. The CPU 10 adopts excessive base-line variation restriction data instead of base-line variation restriction data as data to be displayed.

FIG. 8 is a schematic diagram for describing judgment processing carried out by the CPU 10, for determining whether or not data for excessive base-line variation restriction data is being exhibited or not. Suppose that the average value of the Pb value history is 0 mV in the drawing, lines 1110 and 1111, respectively, representing +0.2 mV and −0.2 mV which become criteria of selecting data. The cardiogram waveform shown in the drawing is a waveform represented by base-line variation restriction data. The CPU 10 adopts the base-line variation restriction data as an object to be displayed because the cardiogram waveform (one cardiac beat) shown in FIG. 8A is between the lines 1110 and 1111. On the other hand, the CPU 10 adopts the excessive base-line variation restriction data as an object to be displayed because the cardiogram waveform (one cardiac beat) shown in FIG. 8B is outside of lines 1110 and 1111.

The excessive base-line variation restriction data is generated with the excessive base-line variation restricting filter 18 by which higher frequency components than the base-line variation restricting filter 17 are cut. Consequently, a cardiogram waveform represented by excessive base-line variation restriction data is displayed in a form that its base-line variation is more restricted than one that represented by the base-line variation restriction data (for example, it is assumed to display so that P value approaches to the vicinity of 0 electric potential)

The processing executed in steps S552 through S558 may utilize values from other recognition points including the recognition point Qb (a value related to Q-wave). In general, it is preferred to adopt recognition points that have less variation among different cardiac beats. The processing executed in step S554 may use a history of an arbitrary number of cardiac beats, except for ten times of cardiac beats. The processing executed in step S554 may also use an arbitrary value, not an average value, which includes the maximum value, minimum value of recognition values within a predetermined range of a cardiac beat. The processing executed in step S558 may use a reference value other than 0.2 mV.

The CPU 10 records the base-line variation restriction data (a) for one cardiac beat containing the point Pb acquired in step S550 into the memory 19 as display waveform data when the Pb tolerance is not greater than 0.2 mV in the processing executed in steps S558 of FIG. 13 (S560). On the contrary, the CPU 10 calculates a value that is reduced 200 from the data number (information on generation sequence) of the base-line variation restriction data (a) for one cardiac beat containing the point Pb acquired in step S550 when it is judged that the Pb tolerance is greater than 0.2 mV, and makes the calculation result as a changed display data number (information on generation sequence specifying the second corrected waveform data after change) (S562). Such calculation will be described later. The CPU 10 acquires the excessive base-line variation restriction data (b) for one cardiac beat containing the changed display data number (S564). The CPU 10 records into the memory 19 the acquired excessive base-line variation restriction data (b) as display waveform data (S566).

Figure 10:
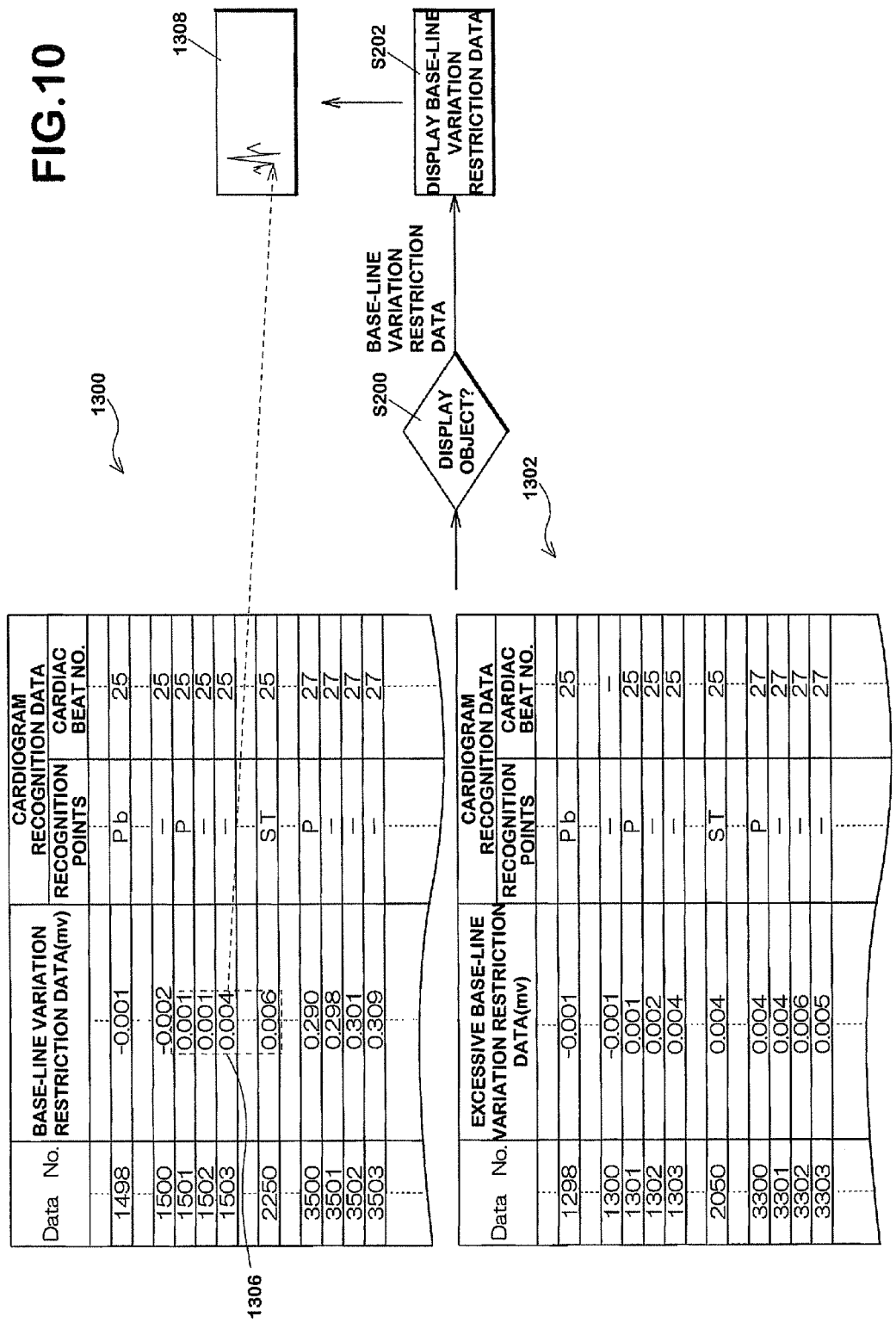
FIG. 10 is a schematic diagram illustrating processing when the base-line variation restriction data is adopted as an object to be displayed.

FIG. 10 is a schematic diagram showing processing for adopting the base-line variation restriction data as display waveform data (see step S560 of FIG. 13). Base-line variation restriction data 1300 and excessive base-line variation restriction data 1302 are stored in the memory 19. The CPU 10 makes a judgment on display object data of cardiogram (step S200, processing corresponding to steps S550 through S558 of FIG. 13). The display object data is one of data 1306 contained on the base-line variation restriction data 1300 and excessive base-line variation restriction data (contained in the excessive base-line variation restriction data 1302) generated by affecting the excessive base-line variation restricting filter 18 to the cardiogram waveform data used for generating the data 1306. When the base-line variation restriction data is selected as the display object data, the CPU 10 displays on the display screen 1308 a cardiogram in accordance with the data 1306 (S202).

Figure 11:
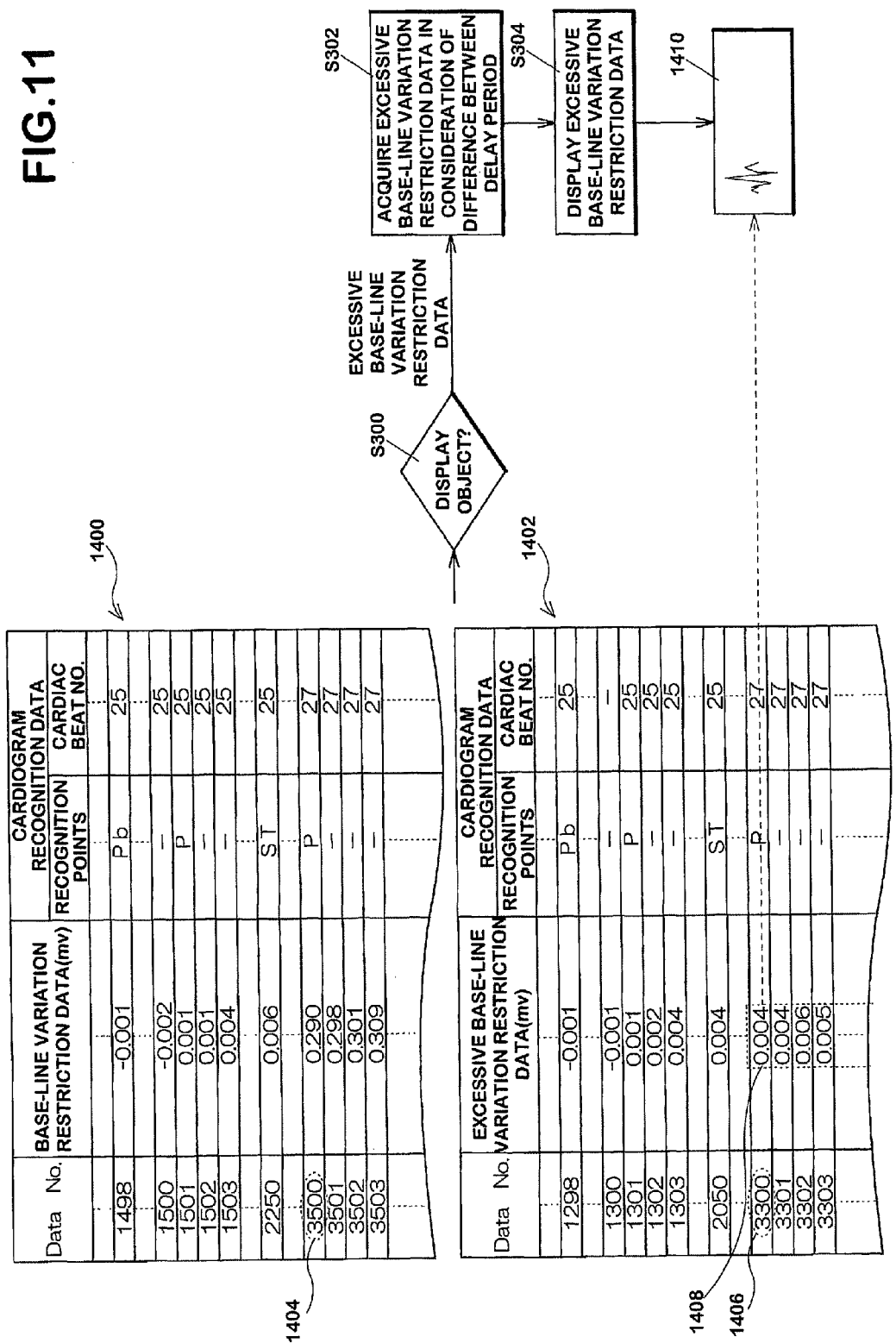
FIG. 11 is a schematic diagram illustrating processing when the excessive base-line variation restriction data is adopted as an object to be displayed.

FIG. 11 is a schematic diagram showing the process of adopting the excessive base-line variation restriction data as data to be displayed (see steps S562, S564 and S566 of FIG. 13). Both base-line variation restriction data 1400 and excessive base-line variation restriction data 1402 are stored in the memory 19. The CPU 10 judges display object data of the cardiogram (processing corresponding to step S300, steps S550 through S558 of FIG. 13). The drawing shows an example of judging display object data on the base-line variation restriction data containing data 1404 (data number "3500") for one cardiac beat. When the base-line variation restriction data is selected as the display object data, the CPU 10 acquires excessive base-line variation restriction data in consideration of a difference between a delay period (time needed for generating the first corrected waveform data) of the base-line variation restricting filter 17 and that (time needed for generating the second corrected waveform data) of the excessive base-line variation restricting filter 18 (S302). In the embodiment, the delay period of the base-line variation restricting filter 17 is 1200 msec, that of the excessive base-line variation restricting filter 18 is 400 msec. Consequently, the difference between both is 800 msec. The measurement period of both the base-line variation restriction data for one cardiogram beat and the excessive base-line variation restriction data for one cardiogram beat are in a unit of 4 msec. As described in the above, a difference of 200 (=800 msec/4 msec) arises between the base-line variation restriction data and the excessive base-line variation restriction data as a data number (or the step number). More specifically, the excessive base-line variation restriction data as to the same cardiac beat of a cardiogram waveform represented by the base-line variation restriction data of data number X (information on generation sequence for specifying the first corrected waveform data) corresponds to data number X-200 (information on generation sequence for specifying the second corrected waveform data). FIG. 11 shows an example of steps performed by the CPU 10 in which a data number 3300 (=3500−200) is calculated (see step S562 of FIG. 13) based on the data 1404 (data number "3500") corresponding to a recognition point P and in which excessive base-line variation restriction data 1408 for one cardiac beat including data 1406 corresponding to the above data number 3300 is acquired. The CPU 10 displays on the display screen 1410 a cardiogram based on the data 1408 (S304).

By carrying out the above steps, the CPU 10 sequentially records one of the base-line variation restriction data and the excessive base-line variation restriction data for displaying a cardiogram for one cardiac beat (see steps S560, S566 of FIG. 13). In this way, the display sequentially displays a cardiogram waveform in time order. At that time, the CPU 10 displays on the display feature values of the cardiogram waveform, in addition to the waveform. When the base-line variation restriction data is used for the display, feature values based on the base-line variation restriction data is displayed, and feature values based on the excessive base-line variation restriction data is displayed when the excessive base-line variation restriction data is used for the display. Averaged feature values for plural cardiac beats (for example 10 beats) may be displayed instead of displaying data of each cardiac beat.

The CPU 10 judges whether or not the measurement ends (S568). If the measurement has not ended, the steps after S500 will be carried out again. For smooth display, recognition is made from the display.

In the embodiment, measurement and display are carried out in a real-time basis. However, recognition and display can be carried out after recording all the cardiogram waveform data from start to end of a measurement.

In the embodiment, comparison between the Pb value of the base-line variation restriction data and history thereof is shown as processing for selecting display object. As another embodiment, it is possible to judge adoption of excessive base-line variation restriction data by comparing the Pb value of the base-line variation restriction data with that of the excessive base-line variation restriction data. Specifically, the CPU 10 acquires excessive base-line variation restriction data by performing steps S562, S564 after execution of step S552 of FIG. 13. The CPU 10 acquires the Pb value in the base-line variation restriction data The CPU 10 adopts the excessive base-line variation restriction data as display waveform data when the difference between the Pb value of the base-line variation restriction data and that of the excessive base-line variation restriction data is greater than a predetermined value (for example 0.2 mV).

4-2. Display

Figure 15:
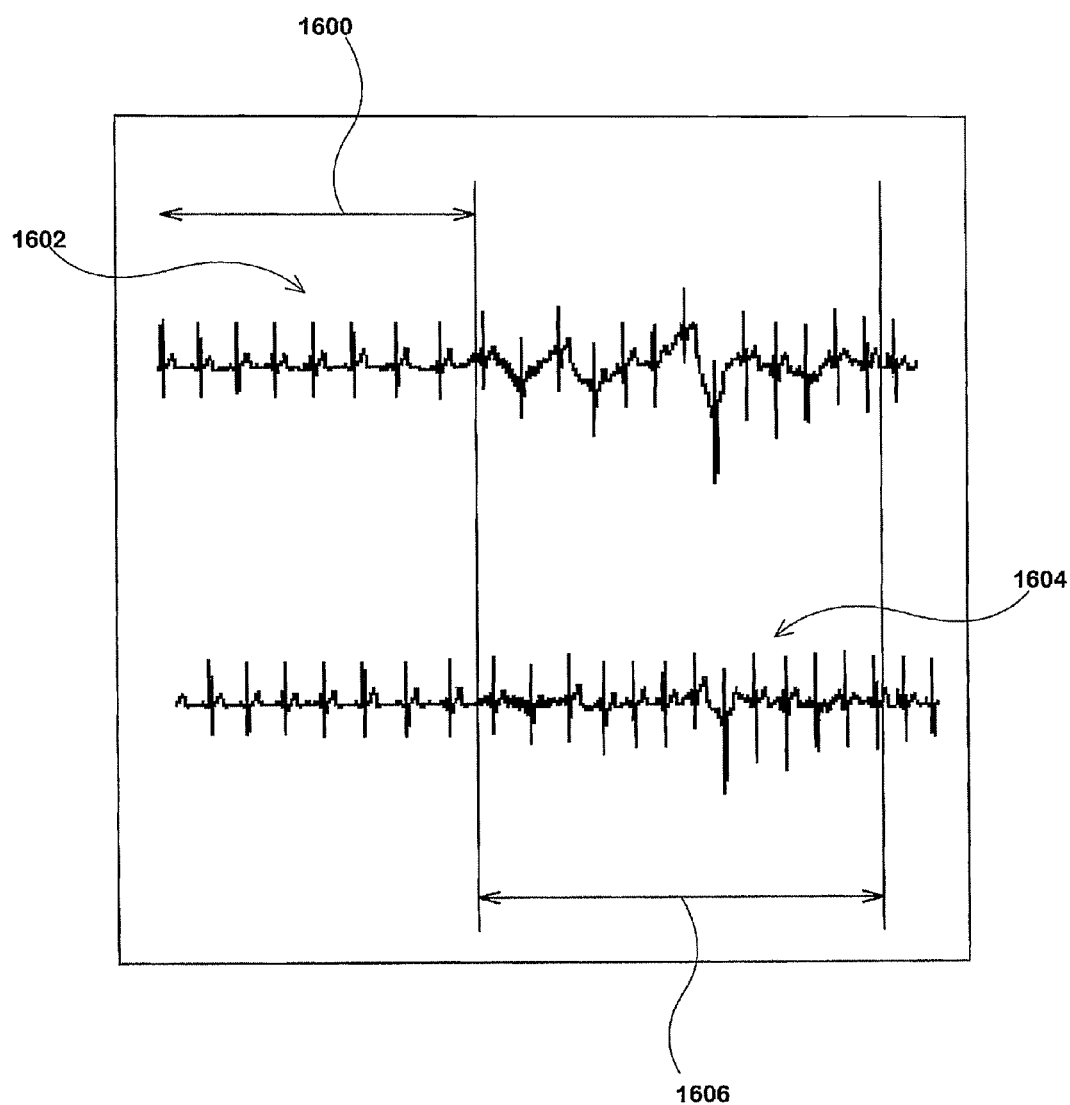
FIG. 15 is a diagram for describing base-line variation restricting waveforms and excessive base-line variation restricting waveforms.

FIG. 15 is a diagram for describing both a base-line variation restricting waveform represented by the base-line variation restriction data and an excessive base-line variation restricting waveform represented by the excessive base-line variation restriction data. Notable variation is observed in segment 1606 on base-line variation restricting waveform 1602. It is difficult to recognize the shape of the cardiogram waveform of a user and variation of recognition values and the like over time during the segment. On the other hand, higher frequency components (for example body movement) than the base-line variation restricting waveform 1602 is cut-off in excessive base-line variation restricting waveform 1604, and the variation of the base-line is restricted in the segment 1606. For example, the CPU 10 displays the base-line variation restricting waveform 1602 for the segment 1600 and display the excessive base-line variation restricting waveform 1604 for the segment 1606 by carrying out the program shown in the flowcharts of FIGS. 12 and 13.

FIG. 16 illustrates examples output to the display 15 as a result of carrying out processing shown in steps S560 and S566 of FIG. 13. On the screen, a cardiogram waveform according to the base-line variation restriction data and another cardiogram waveform according to the excessive base-line variation restriction data are displayed in time order. Bar-marks 1703 and 1705, respectively, indicate that cardiogram waveforms are displayed over the segments. Such bar-marks may be omitted in other embodiment(s). Drawing of the cardiogram with the CPU 10 is carried out by moving (from right to left on the screen) plotting points with the progress of the measurement period. In the embodiment, the longitudinal axis of the display area of cardiogram waveform represents electric potential (millivolts (mV)), and the horizontal axis thereof represents time (second). The actual display area of cardiogram waveform on the display 15 has a ratio of 1 mV=1 centimeter (cm) in the longitudinal axis and, 1 second=25 millimeters (mm) in the horizontal axis. Cardiogram waveforms are drawn (plotted) from right to left on the display area with the progress of measurement period of the cardiogram. The CPU 10 also displays average values of ST levels for every 10 cardiac beats as display waveform recognition data (see step S570 of FIG. 13). In particular, the ST level 1700 (-0.004 mV) to be displayed is an average value of the ST levels for every 10 cardiac beats that is shown as an area symbol 1702. When data on excessive base-line variation restriction is used for that of 10 cardiac beats, characters such as "excessive restriction" can be displayed together with feature values (such as ST levels) (see FIG. 16). In this way, it is possible to attract an operator's attention.

The CPU 10 can acquire information on the ST level in accordance with display waveform recognition data acquired at step S570 of FIG. 13. The ST level is based on STj, ST60 (60 milliseconds behind the STj), ST80 (80 milliseconds behind the STj), and so on. The ST level 1700 and the area symbol 1702 are drawn with the progress of display of the cardiogram waveforms from left to right on the display area. It is possible to display waveform recognition data other than the ST level on the display 15 and possible to omit display of the display waveform recognition data.

4-3. Wave Jointing

According to processing carried out at steps S60 and S566 of FIG. 13, there are places where excessive base-line variation restricting waveforms are displayed following the base-line variation restricting waveforms (and vice versa) in the displayed cardiogram waveforms. Generally, the ending-point of the base-line variation restricting waveforms (for example, a position 100 milliseconds behind the recognition point of a T-wave) and the starting-point of the excessive base-line variation restricting waveform ((for example, a position 100 milliseconds ahead of the recognition point of the P-wave) do not continue because both waveforms are generated by carrying out filtering processing. In the embodiment, in order to maintain their continuity, arbitrarily adoptable processing that will be described hereinafter is executed.

Figure 14A:
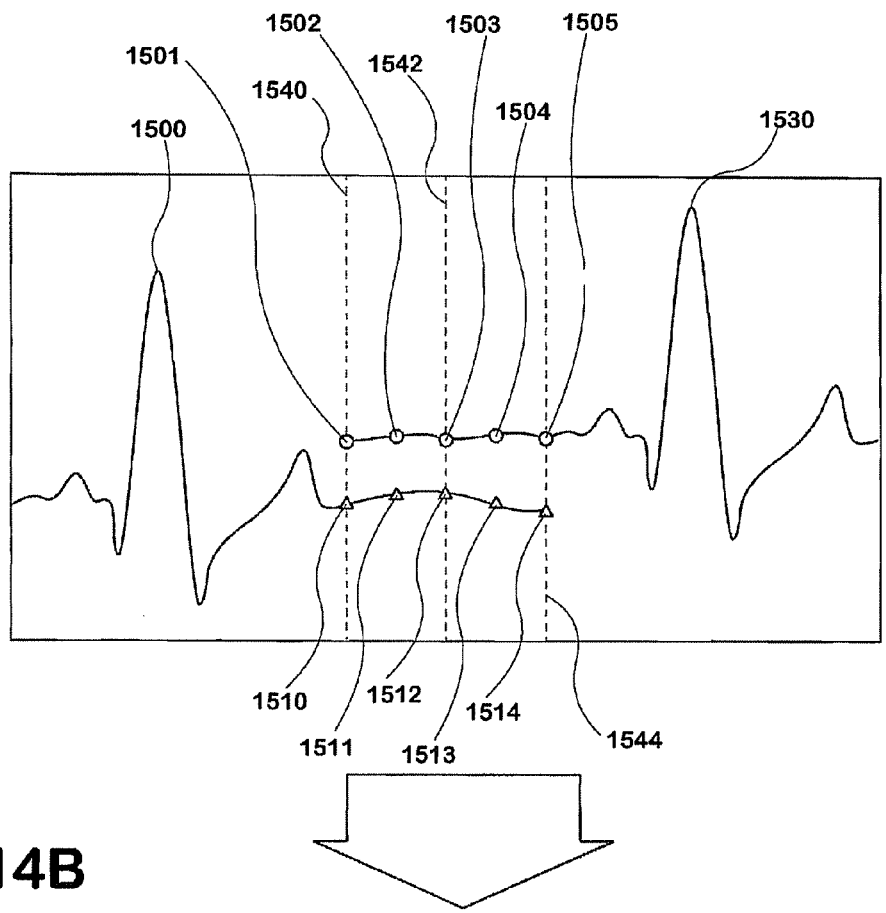
FIGS. 14A and 14B are diagrams for schematically describing an example of display processing for displayed waveforms.
Figure 14B:
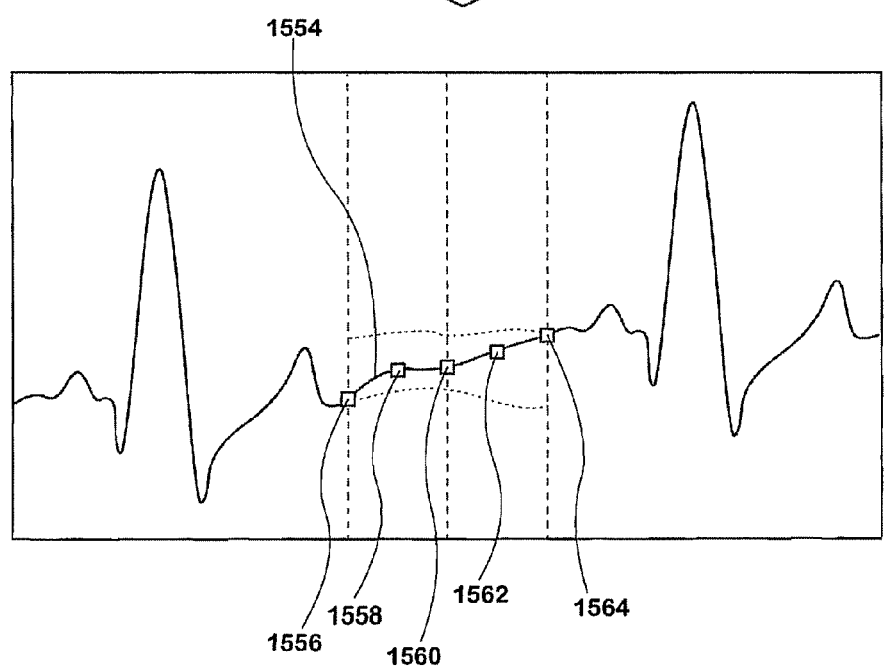

The CPU 10 carries out display processing as schematically illustrated in FIG. 14 after execution of step S568 of FIG. 13. FIG. 14 shows overall processing for maintaining continuity between a waveform 1500 (for example, a base-line variation restricting waveform) and another waveform 1530 (for example, an excessive base-line variation restricting waveform). In particular, the CPU 10 carries out window processing that will be described below for waveforms within a segment ahead and behind 100 milliseconds, mainly on ahead of 100 milliseconds of a P wave.

The CPU 10 sets a position 1542 located at 100 milliseconds ahead of the recognition point P of the waveform 1530 as the center of the wave joining process. Position 1540 is a position located at 100 milliseconds ahead of the position 1542 and position 1544 is a position located at 100 milliseconds behind of the position 1542. The CPU 10 generates data representing a jointed waveform 1554 (see FIG. 14B) within a segment from the position 1540 to the position 1544 by weighting on each waveform point of the waveform 1500 and the waveform 1530 within the segment. The CPU 10 determines values (measurement unit: mV) of each wave point of the jointed waveform 1554 by carrying out the following calculations, for example.

Waveform point 1556=(waveform point 1510*1.0)+ (waveform point 1501*0)

Waveform point 1558=(waveform point 1511*0.75)+ (waveform point 1502*0.25)

Waveform point 1560=(waveform point 1512*0.50)+ (waveform point 1503*0.50)

Waveform point 1562=(waveform point 1513*0.25)+ (waveform point 1504*0.75)

Waveform point 1564=(waveform point 1514*0)+(waveform point 1505*1.00)

A jointed waveform 1554 is displayed by carrying out linear interpolation for waveform points 1556, 1558, 1560, 1562 and 1564, for example (dashed lines used for reference illustrate waveforms prior to joint).

5. Second Embodiment 5-1. Program Flowchart

Figure 17:
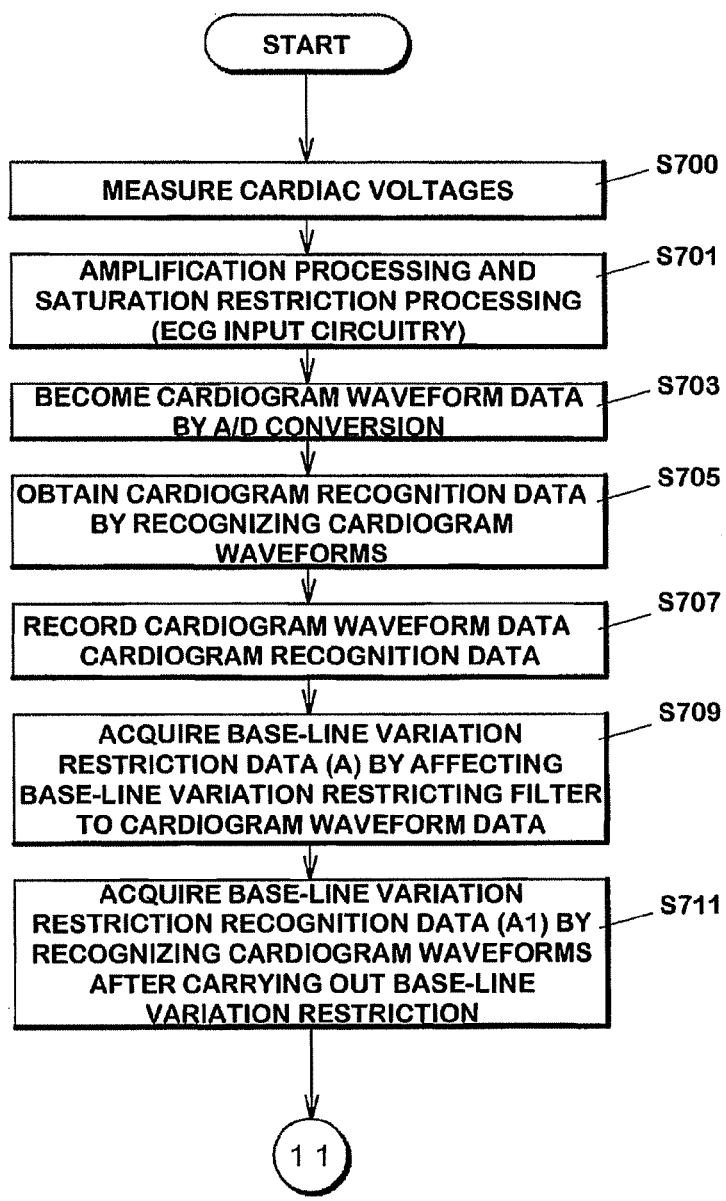
FIG. 17 is a flowchart of an electrocardiogram display processing program according to a second embodiment.
Figure 18:
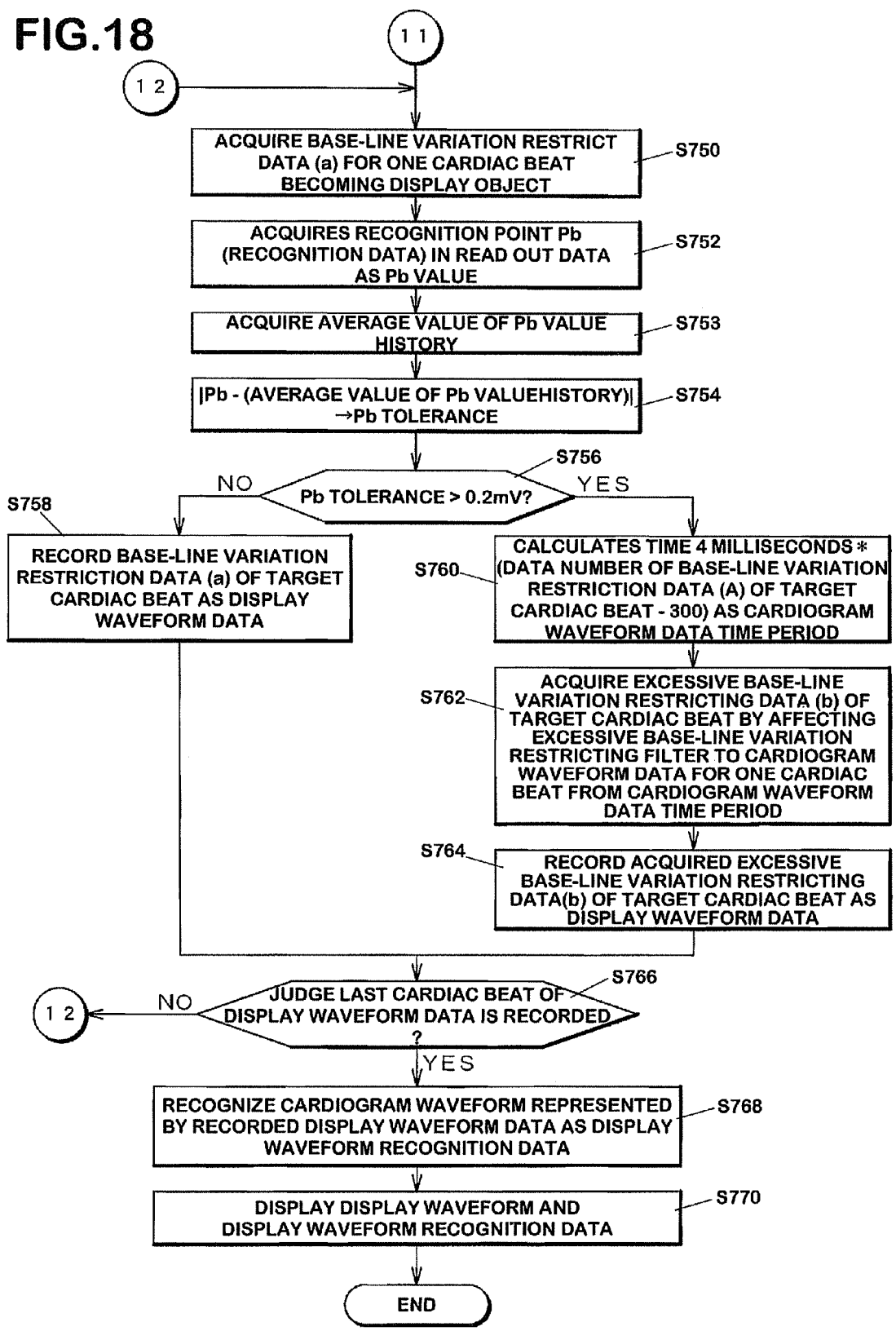
FIG. 18 is another flowchart of the electrocardiogram display processing program according to the second embodiment.

FIGS. 17 and 18 are flowcharts of a cardiogram display processing program according to the second embodiment. In the second embodiment, the CPU 10 generates base-line variation restriction data in accordance with cardiogram waveform data, and generates excessive base-line variation restriction data only for a portion where variation of a base-line is notable. In this regard, this embodiment differs from the first embodiment in which the base-line variation restriction data and the excessive base-line variation restriction data are generated for cardiogram waveform data during a period starting from measuring the cardiogram to a period finishing the measuring of the cardiogram. Although, display is carried out in a real-time basis in the first embodiment, cardiogram waveform data is stored once and is read out for recognition and display in the second embodiment. Needless to say, it is possible to carry out real-time display in the second embodiment.

A flowchart of a cardiogram display processing program according to the second embodiment will be described hereinafter.

The CPU 10 of a cardiogram monitoring device 100 measures the cardiogram (step S700) and carries out each of the following processing: amplification and filtering correction (S701), AD conversion (S703), waveform recognition (S705), recording cardiogram waveform data and cardiogram recognition data (S707), generation of base-line variation restriction data with the base-line variation restricting filter 17 (S709) and acquisition of the base-line variation restriction data (S711).

The CPU 10 reads out from the memory 19 the base-line variation restriction data (a) corresponding to a range for one cardiac beat that becomes an object to be displayed (step S750 of FIG. 18). Then the CPU 10 acquires the base-line variation restriction data at the recognition point Pb in the data being read out as a Pb value (S752). Further, the CPU 10 acquires an average value of Pb value history (S753). The CPU 10 calculates an absolute value in difference (Pb tolerance) between the acquired Pb value in step S752 and an averaged value of the acquired Pb history values in step S753 (S754). The CPU 10 judges whether or not the calculated Pb tolerance is greater than 0.2 mV (S756).

The CPU 10 records the base-line variation restriction data (a) acquired in step S750 into the memory 19 as display waveform data when it judges that the Pb tolerance is not greater than 0.2 mV (S758). On the contrary, when it is judged that the Pb tolerance is greater than 0.2 mV, the CPU 10 calculates a time multiplying 4 milliseconds by the value that reduced 300 from the data number of the base-line variation restriction data (a) acquired in step S750 as cardiogram waveform data time period (S760). In the embodiment, the base-line variation restriction data approximately delays for 300 (=1200 milliseconds/4 milliseconds) steps in comparison with the cardiogram waveform data because a delay time period of the base-line variation restricting filter 17 is 1200 milliseconds. Consequently, it is possible to obtain a measurement time period of cardiogram waveform data (unit: milliseconds) used for generating the base-line variation restriction data (a) by calculating the time multiplying 4 milliseconds by the value that reduced 300 from the data number of the data (a). For example, data 1404 of FIG. 11 (data number: 3500) is data generated by affecting the base-line variation restricting filter 17 to the cardiogram waveform data from measurement time period 12800 milliseconds (=3500-300)*4).

The CPU 10 acquires excessive base-line variation restriction data (b) by affecting the excessive base-line variation restricting filter 18 to the cardiogram waveform data corresponding to a range for one cardiac beat from the cardiogram waveform data time period (S762). In the case of the base-line variation restriction data (a) containing data 1404 of FIG. 11, the excessive base-line variation restriction data (b)(data containing data 1406 of FIG. 7 (data number: 3300)) is acquired by affecting the excessive base-line variation restricting filter 18 to the cardiogram waveform data from measurement time period 12800 milliseconds. The data number "3300" of the data 1406 identify with a value adding 100 (=a delay time period 400 milliseconds of the excessive base-line variation restricting filter 18/4 milliseconds) to the step number 3200 (=measurement time period 12800 milliseconds/4 milliseconds).

The CPU 10 records the acquired excessive base-line variation restriction data (b) in the memory 19 as display waveform data (S764). Then the CPU 10 judges whether or not the last cardiac beat of the display waveform data at the end of measurement is recorded (S766). If no record is made on the last cardiac beat of the display waveform data, the CPU 10 acquires display waveform data for the subsequent cardiac beat by processing executed from step S750. The CPU 10 recognizes feature values of the cardiogram waveform represented by the recorded display waveform data and records them in the memory 19 as display waveform recognition data by carrying out similar processing in step S511 of FIG. 12 when it is judged that the last cardiac beat of the display waveform data is recorded (S768). The CPU 10 displays on the display 15 a display waveform represented by the display waveform data recorded in the memory 19 and the display waveform recognition data and ends the process (S770).

6. Advantages of the Embodiments

In the embodiments, the cardiogram monitoring device 100 generally displays base-line restricting waveforms and displays on the screen excessive base-line restricting waveforms for the segment where much variation is observed (see FIGS. 15 and 16). A user of the device can confirm that continuity of the waveforms is maintained and the cardiogram waveforms with stable base-lines thereof. It is advantageous in that visibility of cardiogram waveforms is increased and variation in feature values of the cardiogram waveforms is decreased.

In general, display continuity of cardiogram waveforms is the only requirement for conventional cardiogram monitoring devices, not enough attention has been paid for display accuracy of waveforms, nor easy-conformation of temporal variation on feature values of waveforms. On this point, the cardiogram monitoring device 100 according to the embodiment considers both the display continuity of cardiogram waveforms and the display accuracy of waveforms. As a result, user reliability for the display increases.

A cut-off frequency 1.45 Hz is shown as a basic feature of the excessive base-line variation restricting filter 18 in the embodiments. With this cut-off frequency, there might be possibility of attenuating a part of the frequency band component (for example, a T wave component). On the other hand, values at the ST-segment generally become highly inaccurate when base-line variation noises caused by body movement are superposed on the cardiogram. It is advantageous in that attenuation at the ST-segment is suppressed to a certain degree by utilizing the excessive base-line variation restricting filter 18 and values at the ST-segment can be displayed as accurately as possible to the user. Bar marks are additionally displayed for the segment where the cardiogram originated from the excessive base-line variation restricting filter 18 is displayed thereon (see bar marks 1703 and 1705 of FIG. 16). With the bar marks, the user can recognize that the cardiogram is originated from the excessive base-line variation restricting filter 18 and/or there might be a situation (for example, body movement, a load) that base-line variation occurs.

In the embodiments, filters having a difference in time delay such as the base-line variation restricting filter 17 and the excessive base-line variation restricting filter 18 are used, for example. One aspect of the embodiments is that necessary data can be acquired in consideration of differences in such time delay as a result of carrying out steps S562 and S564 of FIG. 13 (or steps S760 and S762 of FIG. 18). This processing can be omitted if none of the above-mentioned differences in time delay exists.

In the embodiments, an exemplary processing on the display is carried out as display processing for jointing waveforms by focusing around the position 100 msec ahead of the P-wave (see FIG. 14). In this way, waveform joint processing according to the embodiment has an advantage of decreasing the possibility of varying recognition points of the cardiogram by carrying out such joint processing. But joint of waveforms can be carried out at other positions where they may provide less influence to recognition points of the cardiogram waveforms (such as ST-segment).

In the above embodiments, 2 filters are switched as appropriate, but more than 3 filters may be switched in response to feature values, such as Pb.

7. Third Embodiment

In the first and second embodiments, determination of using any one of the filters is made in accordance with waveform values at the feature points. Determination of using any one of the filters is made in accordance with comparison values among waveform data after filtering in the third embodiment. In other words, the third embodiment uses the comparison values among the waveform data after filtering as the feature values representing base-line variation.

Figure 21:
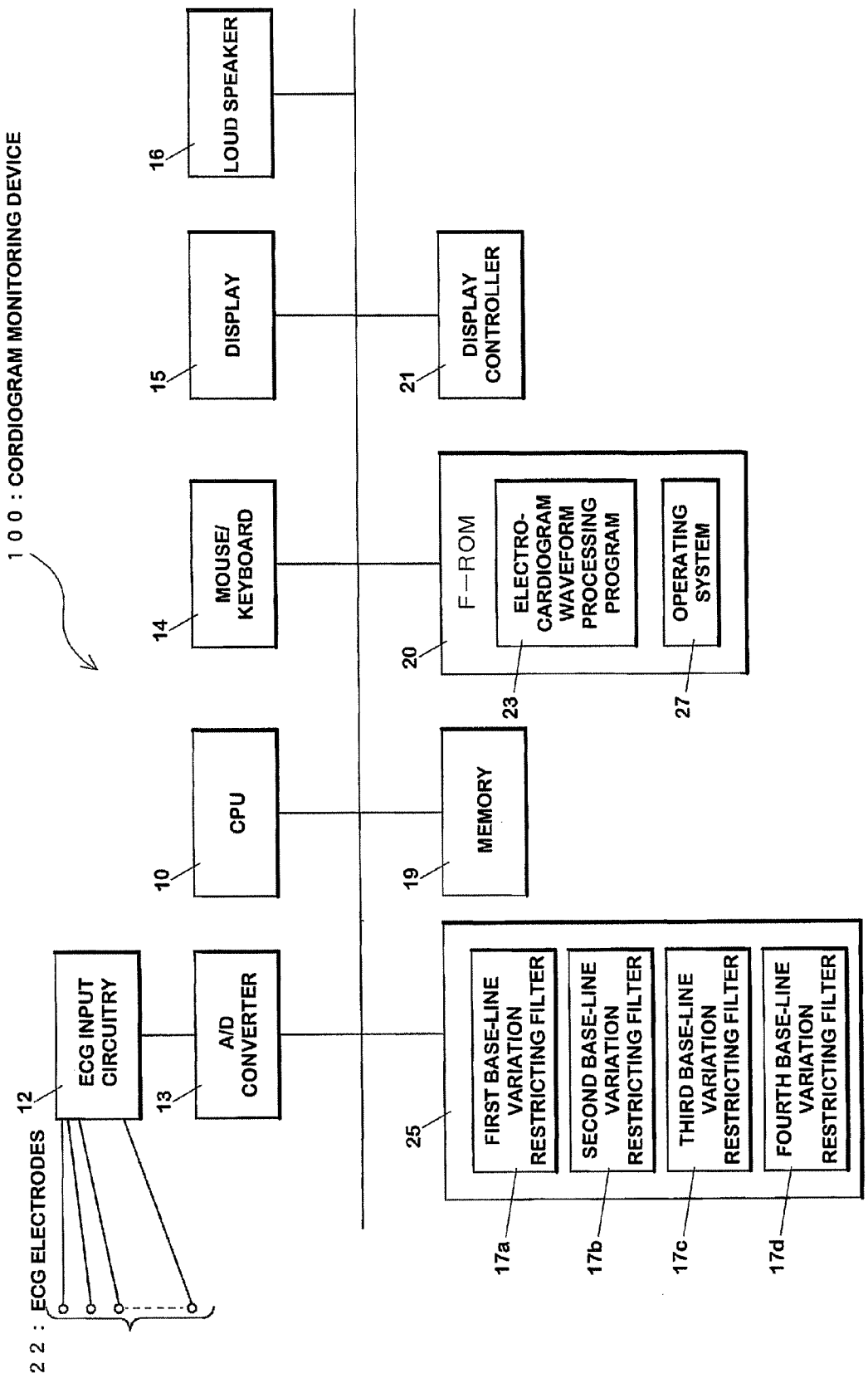
FIG. 21 is a diagram illustrating base-line variation restricting filters 17a through 17d used in a third embodiment.

The hardware structure in the third embodiment is similar to that shown in FIG. 2. As shown in FIG. 21, the first base-line variation restricting filter 17a, the second base-line variation restricting filter 17b, the third base-line variation restricting filter 17c and the fourth base-line variation restricting filter 17d are formed by the DSP 25. These filters have the same basic structure as that shown in FIGS. 5 and 6. In this embodiment, a low cut-off frequency for the first base-line variation restricting filter 17a is set at 0.35 Hz (accuracy of cardiograph defined in JIST 1202), that for the second base-line variation restricting filter 17b is set at 0.5 Hz (accuracy of cardiograph defined in JIST 1304), that for the third base-line variation restricting filter 17c is set at 1.0 Hz and that for the fourth base-line variation restricting filter 17d is set at 1.5 Hz.

Figure 22:
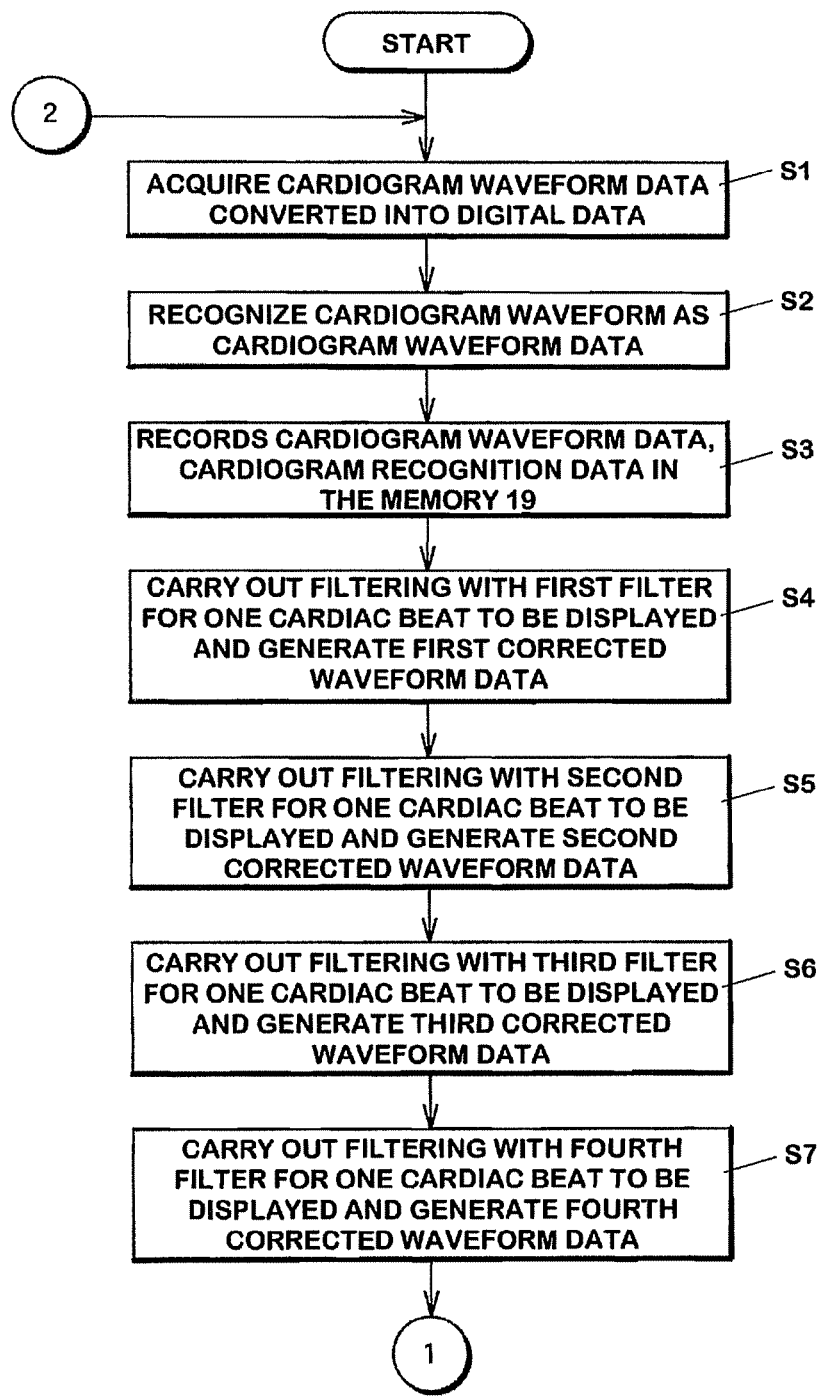
FIG. 22 a flowchart of an electrocardiogram display processing program according to the third embodiment.

FIGS. 22 and 23 are flowcharts of an electrocardiogram display processing program 23 according to the third embodiment. The CPU 10 acquires cardiogram waveform data which is converted into digital data with the A/D converter 13 (Step S1). The CPU 10 may acquire such data by reading out the cardiogram waveform data which is recorded in the memory 19.

Subsequently, the CPU 10 carries out recognition of one cardiac beat, and it recognizes waveform values of the point Pb, the P-wave, the point Qb, the Q-wave, the R-wave, the S-wave, the ST-segment, the ST60 the ST80 and the T-wave as each of feature points in accordance with cardiogram waveform data (step S2). Such recognition may be carried out under the same method as done in the first and the second embodiments. Upon recognizing one cardiac beat and each of the feature points, the CPU 10 records this data in the memory 19 correspondingly with the cardiogram waveform data (step S3).

Figure 29A:
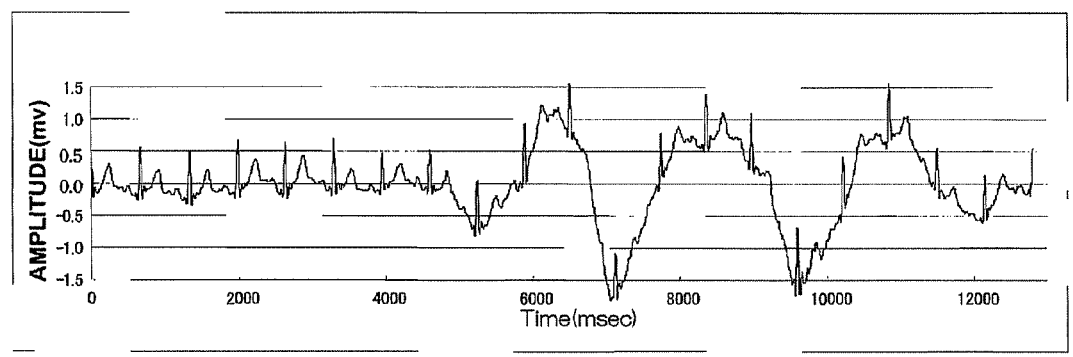
FIGS. 29A, 29B and 29C are graphs showing original waveforms and base-line variation restricting waveforms according to the third embodiment.

FIG. 24 shows the cardiogram waveform data and recognized feature points recorded on the memory 19. The same cardiac beat ID is given to cardiogram waveform data belonging to the same cardiac beat. FIG. 29A schematically shows this cardiogram waveform data (original waveform data).

Thus, cardiogram waveform data, feature points, and so on, are continuously stored in the memory 19. The processing carried out at the steps S1- to S3 may be executed independent from step S4 and later steps.

Subsequently, the CPU 10 reads out the cardiogram waveform data for one cardiac beat as an object from the memory 19, provides it to the DSP 25, carries out filtering with the first base-line variation restricting filter 17a and generates first corrected waveform data (S4). The first corrected waveform data is recorded in the memory 19. FIG. 25 shows the first corrected waveform data recorded in the memory 19. In the graph, cardiac beat ID is also recorded in order to make the corrected data responsive to the original waveform data of FIG. 24.

Similarly, the CPU 10 provides the cardiogram waveform data for one cardiac beat as an object to the DSP 25 and carries out filtering using the second base-line variation restricting filter 17b, the third base-line variation restricting filter 17c and the fourth base-line variation restricting filter 17d, and generates second corrected waveform data, third corrected waveform data and fourth corrected waveform data (steps S5, S6 and S7). The second corrected waveform data, the third corrected waveform data and the fourth corrected waveform data are stored in the memory 19. The format of such data is the same format of the first corrected waveform data.

FIG. 26 schematically shows the first to the fourth corrected waveform data processed by the base-line variation restricting filters 17a through 17d. In the drawings, data on a plurality of beats are shown, the CPU 10 carries out processing on a beat-by-beat basis. As apparent from the drawings, the first base-line variation restricting filter 17a (FIG. 26A) has the lowest restriction against base-line variation, and the base-line variation restricting filter 17b (FIG. 26B), the base-line variation restricting filter 17c (FIG. 26C) and the base-line variation restricting filter 17d (FIG. 26D) have restriction against base-line variation in the order of second lowest to the highest.

Subsequently, the CPU 10 calculates a difference between the fourth corrected waveform data (for one cardiac beat) and the first corrected waveform data (for one cardiac beat) (S8). Similarly, the CPU 10 calculates a difference between the fourth corrected waveform data (for one cardiac beat) and the second corrected waveform data (for one cardiac beat) (S8). The CPU 10 further calculates a difference between the fourth corrected waveform data (for one cardiac beat) and the third corrected waveform data (for one cardiac beat) (S8).

Figure 27A:
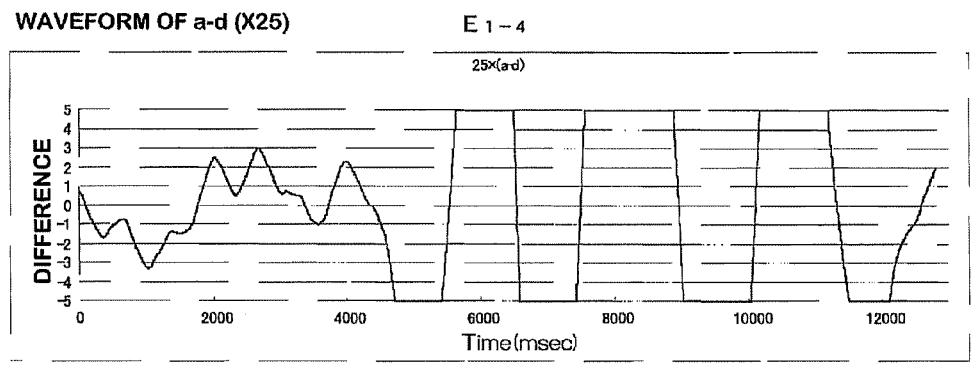
FIGS. 27A, 27B and 27C are graphs showing difference data.
Figure 27B:
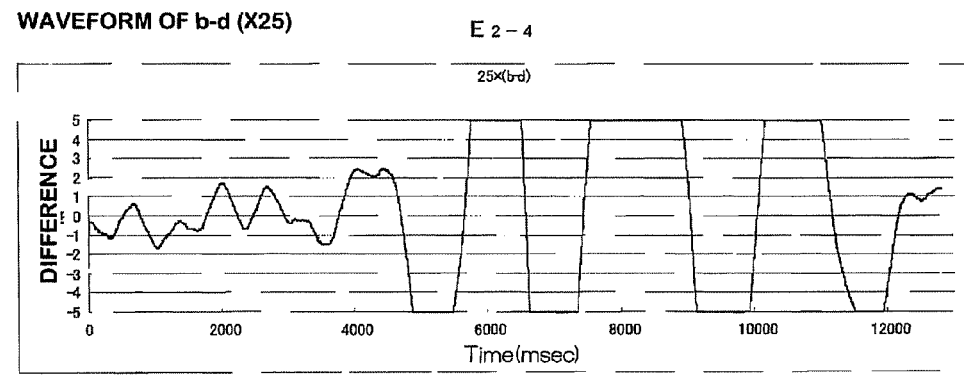
Figure 27C:
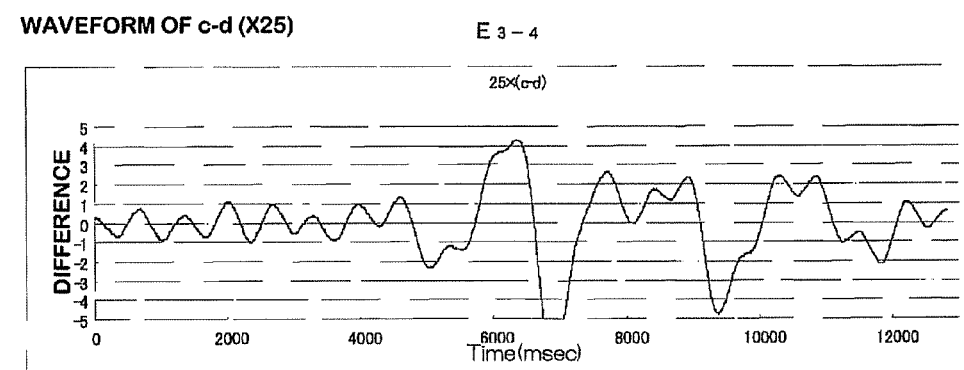

FIG. 27A schematically shows difference data E1-4 of the fourth corrected waveform data and the first corrected waveform data. Similarly, FIG. 27B schematically shows difference data E2-4 of the fourth corrected waveform data and the second corrected waveform data and FIG. 27C schematically shows difference data E3-4 of the fourth corrected waveform data and the third corrected waveform data.

Figure 28A:
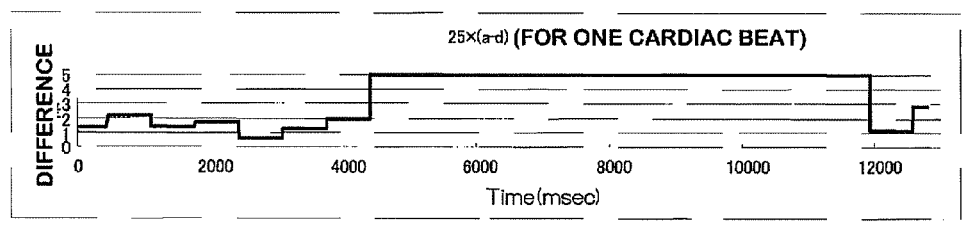
FIGS. 28A, 28B and 28C are graphs showing averaged absolute values for differences.
Figure 28B:
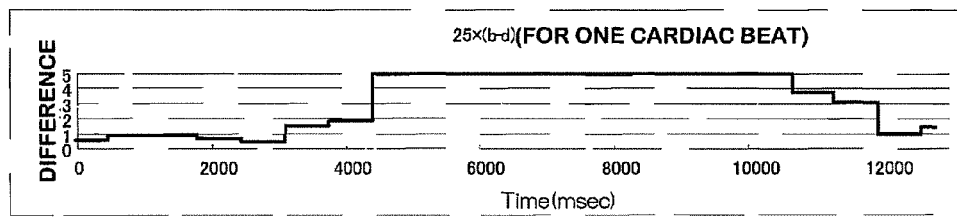
Figure 28C:
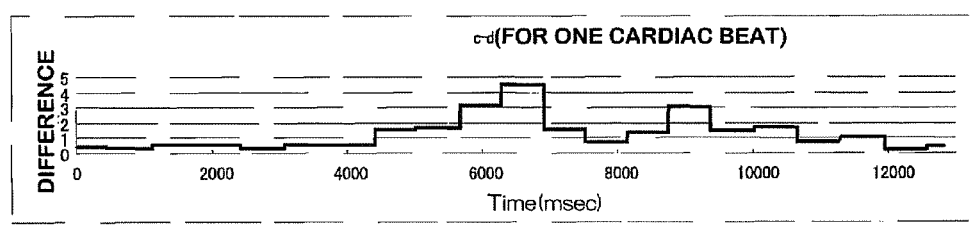

Next, the CPU 10 averages absolute values of difference data ab, bd and cd in the segment for one beat, calculates absolute averages D1-4, D2-4, D3-4 and stores them in the memory 19 (S9). The absolute averages in difference D1-4, D2-4, D3-4 thus calculated are schematically shown in FIGS. 28A, 28B and 28C.

The CPU 10 judges whether or not the absolute average in difference between the values D1-4 is less than a predetermined threshold value (0.4 mV for example) (S10). If, YES, the first corrected waveform data is adopted as display data because the difference between the fourth corrected waveform data and the first corrected waveform data is less than the threshold value (S13). Specifically, the CPU 10 reads out the first corrected waveform data for the one beat from the memory 19 and provides it to the display controller 21. As a consequence, the display controller 21 displays the first corrected waveform data on the display 15.

If the absolute average in difference between the values D1-4 is more than the predetermined threshold value in step S10, the CPU 10 judges whether or not the absolute average in difference between the values D2-4 is less than the predetermined threshold value (S11). If YES, the second corrected waveform data is adopted as display data (S14). Specifically, the CPU 10 reads out the second corrected waveform data for the one beat from the memory 19 and provides it to the display controller 21. As a consequence, the display controller 21 displays the second corrected waveform data on the display 15.

Figure 30:
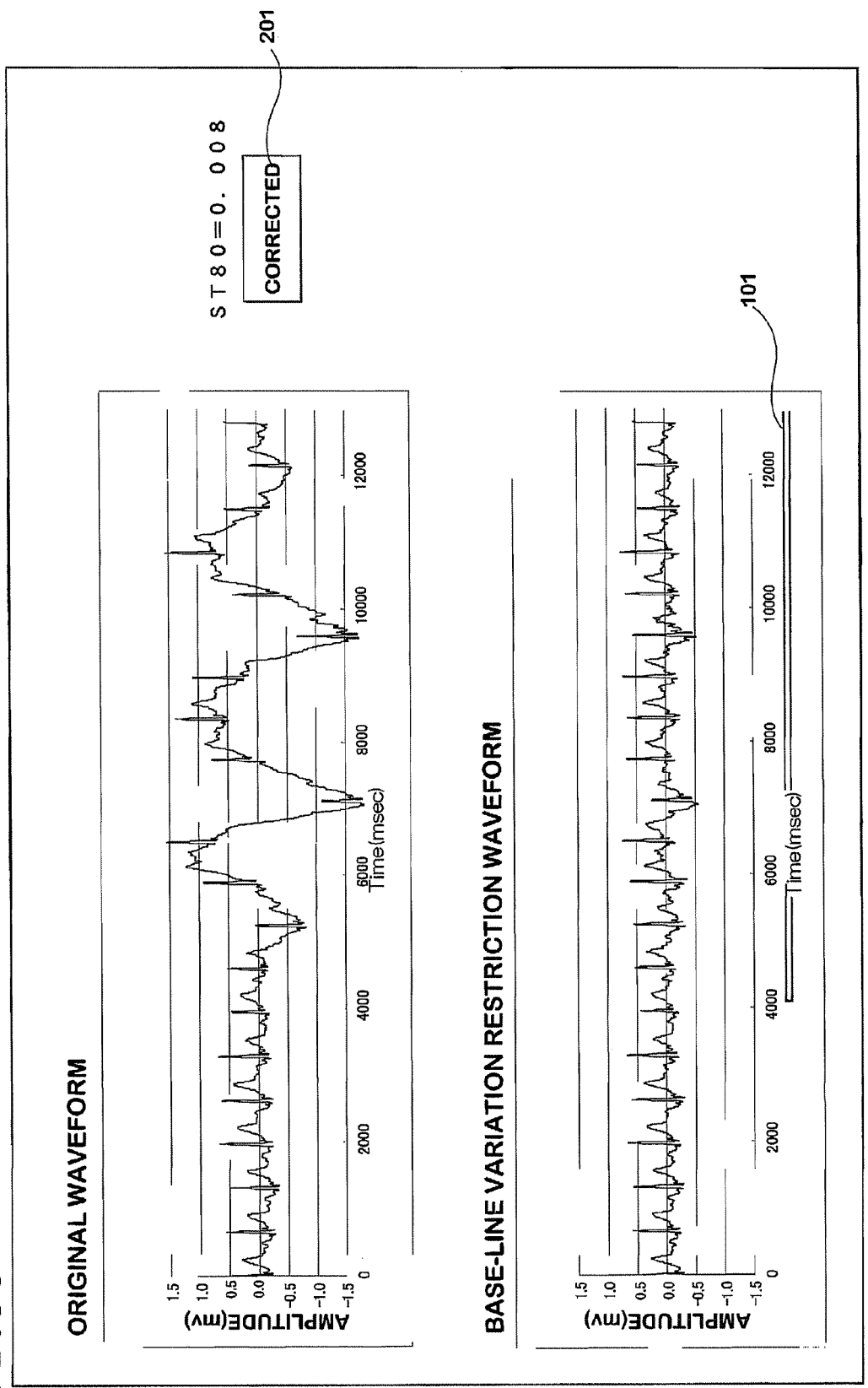
FIG. 30 shows display examples according to the third embodiment.

If the absolute average in difference between the values D2-4 is more than the predetermined threshold value in step S11, the CPU 10 judges whether or not the absolute average in difference between the values D3-4 is less than the predetermined threshold value (S12). If YES, the third corrected waveform data is adopted as display data (S15). Specifically, the CPU 10 reads out the third corrected waveform data for the one beat from the memory 19 and provides it to the display controller 21. As a consequence, the display controller 21 displays the third corrected waveform data on the display 15. At that time, the CPU 10 commands the display controller 21 to display a bar in the vicinity of the waveform data for the one cardiac beat. As a consequence, a bar 101 is displayed as shown in FIG. 30 when the third base-line variation restricting filter 17c and the fourth base-line variation restricting filter 17d are used.

If the absolute average in difference between D3-4 exceeds the predetermined threshold value in step S12, the CPU 10 adopts the fourth corrected waveform data as display data (S16). Specifically, the CPU 10 reads out the fourth corrected waveform data for the one beat from the memory 19 and provides it to the display controller 21. As a consequence, the display controller 21 displays the fourth corrected waveform data on the display 15. At that time, the CPU 10 commands the display controller 21 so that a bar is displayed in the vicinity of the waveform data for the one cardiac beat. As a consequence, the bar 101 is displayed as shown in FIG. 30 when the third base-line variation restricting filter 17c and the fourth base-line variation restricting filter 17d are used.

Subsequently, the CPU 10 reads out a waveform value of a feature point for corrected waveform data being selected which corresponds to a recognized point (ST80, for example) in the original waveform data and commands the display controller 21 to display it (S17). Assuming that the original waveform data is as shown in FIG. 24 and the 25th beat (cardiac beat ID=25) is currently under process, the CPU 10 initially acquires the data number of the feature point of the ST80 from the data shown in FIG. 24. Here, data number "2060" is acquired. Subsequently, the CPU 10 acquires a waveform value of the data number "2060" out of the corrected waveform data (FIG. 25) of the selected base-line variation restricting filter (assuming that the first base-line variation restricting filter 17a is selected). Here, 0.008 is acquired. As a consequence, the waveform value of the ST80 for the beat is displayed as shown in FIG. 30. At that time, for example, display 201 displays "corrected" on the display in order to clarify that the display waveform data is not based on the original waveform data. A display "corrected (excessive restriction)" is made, if corrected waveform data that is processed by a base-line variation restricting filter which does not satisfy Japanese Industrial Standards (JIS) is used.

In this embodiment, the waveform value of the feature point for the corrected waveform data is displayed as a feature value for the supplemental use of diagnosing clinical conditions, the waveform value of the feature point for the original waveform data may also be displayed as the feature value for the supplemental use of diagnosing clinical conditions.

In this embodiment, a display corresponding to time is made not only to the corrected waveform data processed by the selected filter, but also to the original waveform (FIG. 30).

Upon completion of the above described processing, the CPU 10 repeats step S1 and subsequent steps again using an upcoming cardiac beat as an object to be processed.

Figure 29B:
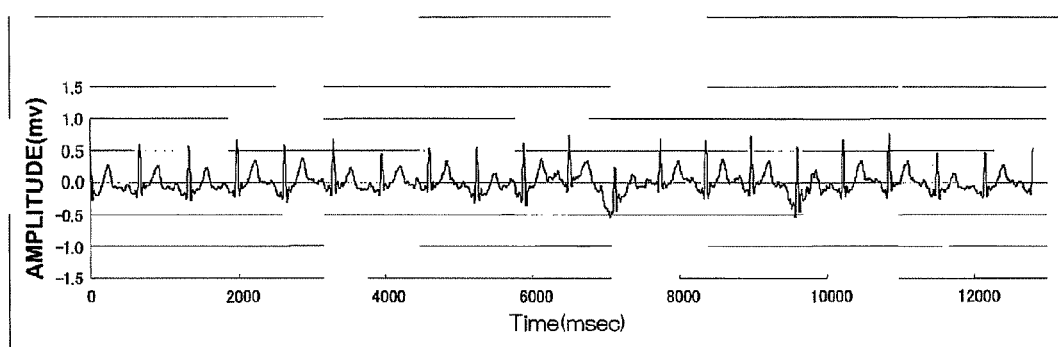
Figure 29C:
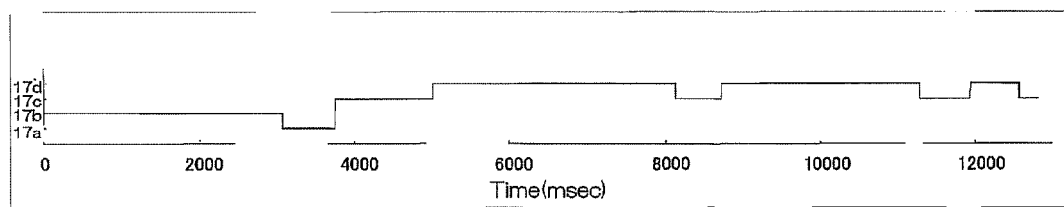

FIG. 29 shows the original waveform data, the waveform to be displayed, a sort of the filter to be selected in the cardiogram waveform display device according to this embodiment. As shown in FIG. 29C, one of the base-line variation restricting filters 17a through 17d is used in a switched manner in response to the degree of base-line variation for the original waveform.

8. Fourth Embodiment

In the above-described embodiments, a total of four base-line variation restricting filters 17a through 17d are used in a switched manner. However, in the case of detecting large variations of the original waveforms such as in a cardiogram waveform of a new-born baby, additional filter(s) may be added. For example, a total of seven base-line variation restricting filters 17a through 17g may be used. The base-line variation restricting filters 17a through 17d used in this embodiment have the same cut-off frequency as that used in the third embodiment. In addition to these four filters, a fifth base-line variation restricting filter 17e (a low cut-off frequency of 2.5 Hz), a sixth base-line variation restricting filter 17f (a low cut-off frequency of 3.5 Hz) and a seventh base-line variation restricting filter 17g (a low cut-off frequency of 5.1 Hz) are installed within the DSP 25.

The method of selecting one of the base-line variation restricting filters is the same as that of the third embodiment. In other words, the CPU 10 calculates average values D1-7, D2-7, D3-7, D4-7, D5-7 and D6-7 of absolute values for the difference between corrected waveform data processed with the seventh base-line variation restricting filter 17g and that processed with the first to the sixth base-line variation restricting filters 17a through 17f.

It is judged that the absolute averages in difference are less than the predetermined threshold value in the order of the absolute averages in difference D1-7, D2-7, D3-7, D4-7, D5-7 and D6-7. In such sequential judgment, selection of a filter is carried out whenever any one of the absolute averages is less than the threshold value. That is, an xth base-line variation restricting filter is selected when the absolute average in difference Dx-7 that is less than the threshold value is found. In the case of the absolute average in difference D6-7, the seventh base-line variation restricting filter 17f is selected if the average value is not less than the threshold value.

Figure 31A:
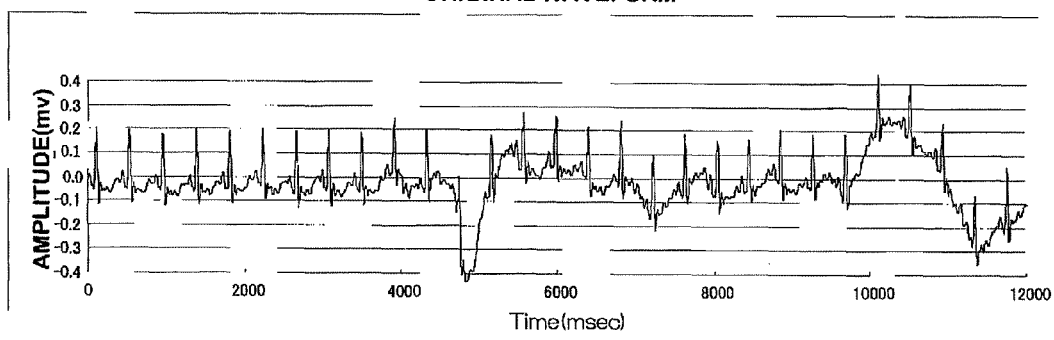
FIGS. 31A, 31B and 31C are graphs showing original waveforms and base-line variation restricting waveforms according to a fourth embodiment.
Figure 31B:
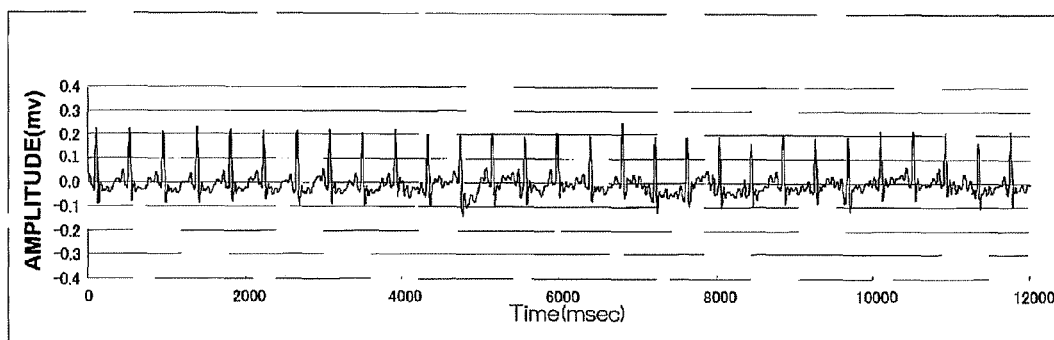
Figure 31C:
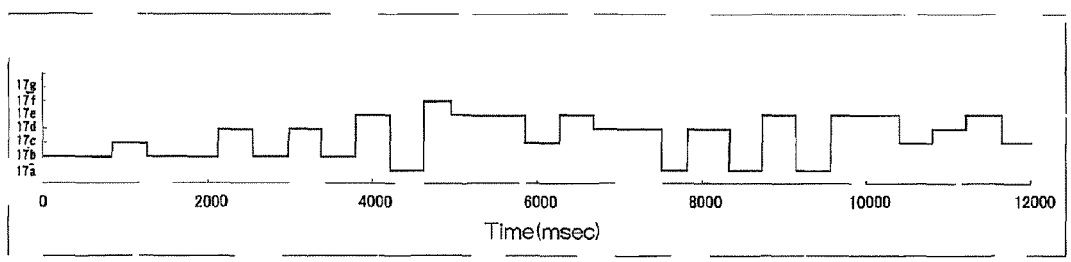

FIG. 31 show examples of base-line variation according to this embodiment. FIG. 31A is waveform data (the original waveform). FIG. 31B shows corrected waveform data obtained through a selection of one of the base-line variation restricting filters 17a through 17f to be appropriate one for each cardiac beat and through the execution of filtering with the selected filters. FIG. 31C schematically shows which one of the filters is selected. As apparent from the drawings, it is understood that the base-line variation restricting filter having a higher low cut-off frequency is selected at portions where large base-line variations are observed.

FIGS. 32 and 33 show effects of base-line variation restriction in the case where base-line variation in the original waveforms is notable. As shown in FIGS. 32A and 33A, there might be a case of detecting large variations of the original waveforms during the measurement of a cardiogram waveform for a new-born baby. As a consequence, there might be the possibility that the original waveforms are displayed out of the display frame (from 0.4 to −0.4 in the drawings) if the original waveforms are displayed as they are.

FIGS. 32B and 33B show corrected waveform data to which base-line variation restriction has been done by this embodiment. As shown in FIGS. 32C and 33C, the base-line variation restricting filters 17a through 17f were selected corresponding to the waveform data.

9. Other Embodiments

An example of displaying cardiogram waveforms on the display 15 as "a cardiogram waveform display object" is described in the embodiments (see steps S560, S566 of FIG. 13, step S770 of FIG. 18 and FIG. 16). As another embodiment, it is possible to adopt any one of the following process such as outputting of the display waveform data displayed in the embodiments (including base-line variation restriction data and/or excessive base-line variation restriction data) to a memory card, a CD-ROM and the like, and outputting to communication means (LAN, Ethernet (Registered Trademark), telephone lines, radio communication, the Internet, cable communication, infrared communication, mobile-phone, Bluetooth, PHS and so on), and outputting display waveform data for file-copying between two devices via a portable medium (for example, writing to a PCMCIA memory card and so on) and outputting cardiogram waveforms represented by display waveform data as a hard-copy or output of a facsimile machine.

As shown in FIG. 16, portions forming excessive base-line variation restriction waveform are displayed with the bar marks so that the portions can be distinguished from the base-line variation restriction waveform in the embodiments. A method of displaying the excessive base-line variation restriction waveform and/or the base-line variation restriction waveform so that they are distinguishable from each other may be altered by means well-known to one skilled in the art. FIG. 19 shows examples of displays output from the execution of the electrocardiogram display processing. FIG. 19A shows a base-line variation restriction waveform 1800 and an excessive base-line variation restriction waveform 1801. Specifically, the waveform 1801 is displayed in a dashed line in order to distinguish waveform 1800 from waveform 1801. FIG. 19B shows a base-line variation restriction waveform and an excessive base-line variation restriction waveform. Specifically, the waveform 1803 represents base-line variation restriction waveform and the waveform encircled by an area 1805 represents an excessive base-line variation restriction waveform.

Although two filters are used in the above-described embodiment, equal or more than three filters may be used. In the case of using three filters, it is possible to display which waveform is obtained using which filter. It is also possible to display whether a waveform is the one output from a filter(s) which meet one of the JIST1202 and JIST 1304 or the one output from a filter(s) carrying out excessive restriction more than the above filter.

Figure 20:
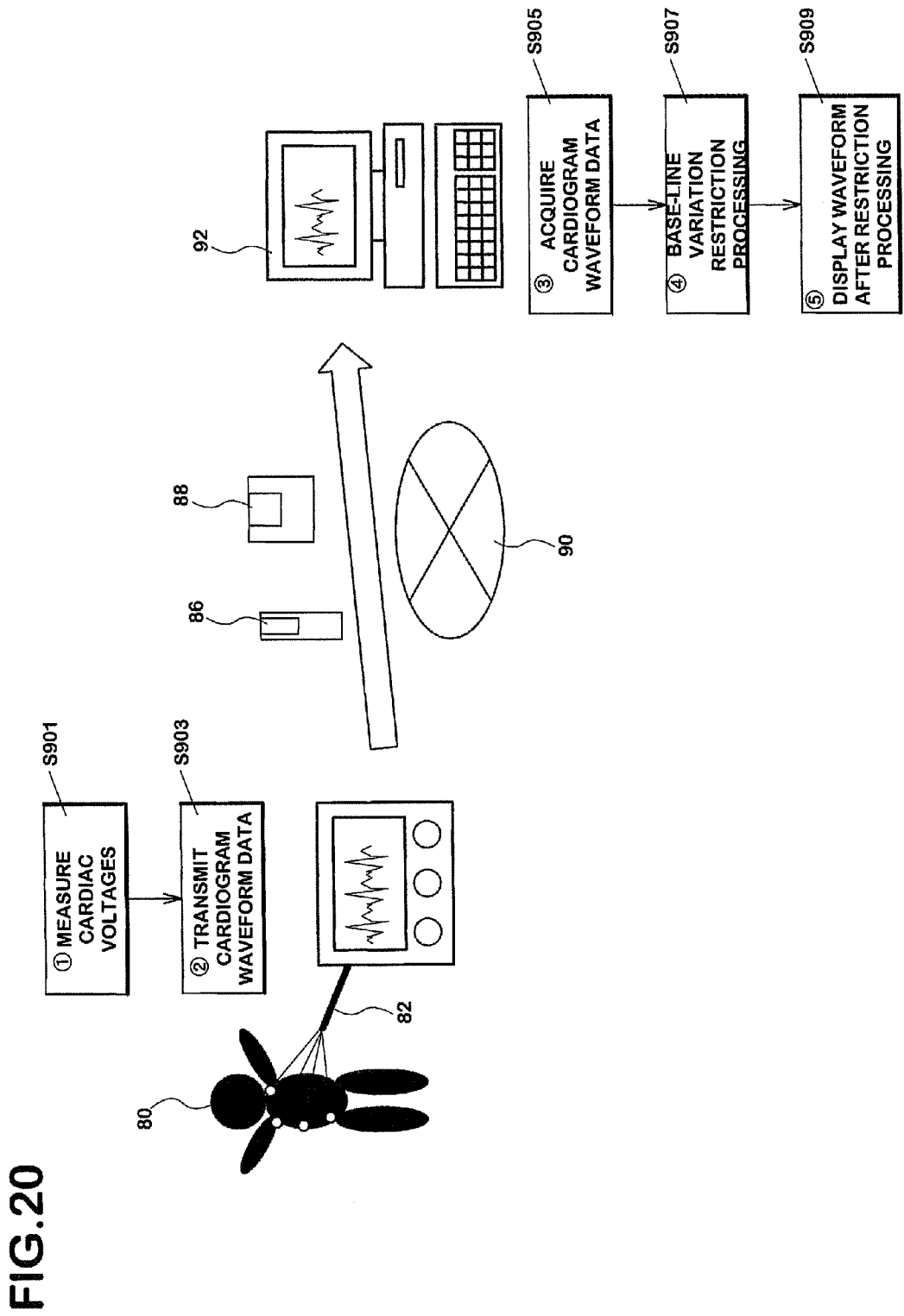
FIG. 20 is a diagram showing another structure of the electrocardiogram monitoring device.

The monitoring device 100 carries out both processing for measuring a cardiogram and displaying thereof in the embodiments. These processes may be performed by equal or more than two independent devices as in the other embodiment. FIG. 20 is a diagram showing another construction of another electrocardiogram monitoring device. An electrocardiogram measuring device 84 measures a cardiogram of an examinee 80 with ECG electrodes 82 and generates cardiogram waveform data. A monitoring device 92, on the other hand, carries out base-line variation restriction processing by acquiring the generated cardiogram data and displays a base-line variation restricted waveform.

In particular, the measuring device 84 measures cardiac voltages (step S901), and transmits the generated cardiogram waveform data (S903). Such processing from the measurement of cardiac voltages to the generation of cardiac waveform data are identical with steps S500 to S507 of FIG. 12. The monitoring device 92 acquires the cardiogram waveform data (S905). Acquisition of the cardiogram waveform data is carried out using communication means including the Internet 90, for example, or using storage medium including a flexible disc 88 or a memory card 86. The monitoring device 92 carries out base-line variation restriction processing on the cardiogram waveform data (S907) and displays the waveform after the restriction processing (S909). Both the restriction and the display processing are identical with steps S509 of FIG. 12 to S572 shown in FIG. 13.

The base-line variation restriction processing carried out by either of the monitoring device 100 and the monitoring device 92 may also be incorporated into viewer software which performs cardiogram display as another embodiment.

Alternatively, a system (a client-server type) connecting client devices transmitting cardiogram waveform data and a server device executing the base-line variation restriction processing using the Internet or a local area network (LAN) may be adopted as another embodiment. For example, such processing may also be processed on a Web-basis utilizing the Internet such as ASP (Application Service Provider) services.

Other embodiments described in the above may be applicable to the embodiments described herein below.

Although the program for operating the CPU 10 is stored in the F-ROM 20 in the embodiments described above, this program may be read out from a CD-ROM recording the program and being installed in a hard disk, or the like. Such program may also be installed from a computer readable data recording medium such as a DVD-ROM, a flexible disc (FD) and an IC card so on other than the CD-ROM. Further, the program can be downloaded through a communication line. Additionally, instead of indirect execution of the program recorded in the CD-ROM with a computer by installing the program from the CD-ROM, direct execution of the program recorded in the CD-ROM may be carried out.

A program executable by a computer meant not only to the one directly executable by installing as it is, but it also includes the one need to be converted once into other format and the like (for example, the one in data compression which is needed for decompression) and includes the one executable after incorporation of other module portion(s).

Determination for which one of the base-line variation restricting filters being used is made in accordance with an averaged value for absolute values of a difference between values in the third and the fourth embodiments. However, such determination may be made in consideration of waveform values at the feature points illustrated in the first and the second embodiments. For example, determination for which algorithm being used is made in accordance with the amount of the waveform values by preparing a plurality of algorithms for selecting a base-line variation restricting filter.

In the above described embodiments, the base-line variation restricting filters are divided into a group satisfying the JIS standard and the other group which does not meet the JIS and a bar is displayed to discriminate both groups. Such display can be made for equal or more than three groups.

The ST80 is displayed as a feature value for supplemental use of diagnosing clinical conditions in the above described embodiments. However, other feature values may also be used as a feature value for supplemental use of diagnosing clinical conditions.

In each of the embodiments described in the above, each function of is realized by the CPU 10 and the program, a part of the whole of such function may be realized by a hardware logic (logic circuitry).

One cardiac beat is considered as a measurement segment in each of the embodiments described in the above, a filter may be switched in accordance with a time period shorter than one cardiac beat or longer (several beats and the like) than one beat both considered as a measurement segment.

In the above described embodiments, waveforms are displayed on the display screen as in the FIGS. 16 and 30, the same result may also be printed by a printer independently or together with the display thereof.

What is claimed is:

1. A cardiogram waveform display device for displaying cardiogram waveforms comprising:
   a waveform data storage portion that stores waveform data which is converted to digital data from cardiogram waveform signals measured with a cardiograph;
   a first to an n th filtering means, for carrying out low frequency cut-off processing of the waveform data stored in the storage portion, and for acquiring a first to an n th corrected waveform data, each of the filtering means having a different cut-off frequency;
   selecting means, for recognizing an amount of variation of a base-line for each of a plurality of segments relative to at least any one of the waveform data and the first to the n th corrected waveform data, and for selecting any one of the first to the n th filters in accordance with the amount of variation of the base-line for each of the segments; and
   display control means for displaying output of the filter selected for each of the segments by the selecting means.

2. A cardiogram waveform display device according to claim 1, wherein the display control means simultaneously displays an output of a filter having a lowest cut-off frequency out of the waveform data or the first to the n th corrected waveform data correspondently with an output of a filter selected by the selecting means.

3. A cardiogram waveform display device according to claim 1, wherein the selecting means recognizes an amount of variation of the base-line by calculating feature values of the waveform data or the corrected waveform data for each of the segments.

4. A cardiogram waveform display device according to claim 3, wherein the selecting means uses a waveform value for at least one of a P-wave, a Q-wave, an R-wave, a S-wave, a ST-segment and a T-wave as the feature values.

5. A cardiogram waveform display device according to claim 4, wherein the selecting means uses a waveform value of a point Pb or a waveform value of a point Qb as the feature values.

6. A cardiogram waveform display device according to claim 4, wherein for larger differences between the waveform value and a reference value, the selecting means selects filtering means having a higher cut-off frequency.

7. A cardiogram waveform display device according to claim 4, wherein the first cut-off frequency is a low cut-off frequency for performing functions of a cardiogram monitoring device as defined in the JIST 1304 standard.

8. A cardiogram waveform display device according to claim 3, wherein the cut-off frequency of the first to n th filters grows sequentially from the first filter, the second filter and up to the n th filter, and wherein the selecting means calculates an average of absolute values in difference between the first to the n th corrected waveform data for each of the plurality of segments as the feature value, and selects one of the filters in accordance with the averaged value in difference.

9. A cardiogram waveform display device according to claim 8, wherein the display control means displays either an output of a filter having a lowest cut-off frequency out of the waveform data or the first to the n th corrected waveform data correspondently with an output of a filter selected by the selecting means.

10. A cardiogram waveform display device according to claim 8, wherein the selecting means calculates average values, of a first to an n−1 th for each of the plurality of segments, of absolute values in difference between the first to the n−1 th corrected waveform data for each of the plurality of segments and selects a filter having a lowest cut-off frequency among values having equal or less than a predetermined reference value in the average values of the first to the n−1 th.

11. A cardiogram waveform display device according to claim 10, wherein the selecting means selects the n th filter when there is no value equal to or less than the predetermined reference value in the average values of the first to the n−1 th.

12. The cardiogram waveform display device according to claim 8, wherein the selecting means carries out selection of a filter using averaged difference values together with waveform values for at least one of the a P-wave, a Q-wave, an R-wave, a S-wave, a ST-segment and T-wave.

13. A cardiogram waveform display device according to claim 8, wherein the first to the fourth filters are provided, each having the first to the fourth cut-off frequency, respectively.

14. A cardiogram waveform display device according to claim 13, wherein the first cut-off frequency is a low cut frequency required by a cardiograph defined in JIST 1202, and wherein the second cut-off frequency is a low cut frequency required by a cardiogram monitoring device defined in JIST 1304.

15. A cardiogram waveform display device according to claim 14, wherein the display control means controls so that the first corrected waveform data processed with the first cut-off frequency, the second corrected waveform data processed with the second cut-off frequency, the third corrected waveform data processed with the third cut-off frequency and the fourth corrected waveform data processed with the fourth cut-off frequency are displayed such that they are discriminable relative to one another.

16. A cardiogram waveform display device according to claim 13, further comprising a fifth to a seventh filters, each having a fifth to a seventh cut-off frequency, respectively.

17. A cardiogram waveform display device according to claim 3, further comprising feature value calculation means for supplemental use of diagnosing clinical conditions which calculates feature values for supplemental use of diagnosing clinical conditions for one of waveform data and corrected waveform data in each of the plurality of segments, wherein the display control means controls to display the feature values for supplemental use of diagnosing clinical conditions.

18. A cardiogram waveform display device according to claim 17, wherein the display control means controls to display feature values for supplemental use of diagnosing clinical conditions in accordance with corrected waveform data processed by the filter selected with the selecting means, and further controls to carry out display for recognizing whether the feature values for supplemental use are based on corrected waveform data excessively restricting its base-line over a range defined in a corresponding JIS standard.

19. A cardiogram waveform display device according to claim 1, wherein the first filtering means has a first cut-off frequency and the second filtering means has a higher cut-off frequency than the first cut-off frequency, and wherein the selecting means selects one of the first filtering means and the second filtering means.

20. A cardiogram waveform display device according to claim 1, wherein the display control means controls to display a display object so that the display object belonging to, either any one of the first corrected waveform data through the n th corrected waveform data or any group of the first corrected waveform data through the n th corrected waveform data being grouped, is identifiably displayed in a manner corresponding to the displayed waveform.

21. A cardiogram waveform display device according to claim 20, wherein the display control means controls to display a bar at a vicinity of the display waveform for each segment thereof, for recognizing whether the displayed waveform is corrected waveform data excessively restricting its base-line over a range defined in a corresponding JIS standard.

22. A cardiogram waveform display device according to claim 1, wherein each of the plurality of segments represents one cardiac beat.

23. A cardiogram waveform display device according to claim 22, wherein the display control means adjusts corrected waveform data, so that the corrected waveform data to be displayed sequentially in accordance with tail waveform data behind a tail of a T-wave of preceding corrected waveform data, and corresponding tail waveform data of subsequent corrected waveform data in precedent cardiogram segments, when continuity of the corrected waveform data to be displayed is lost because precedent corrected waveform data selected for precedent cardiogram segments and subsequent corrected waveform data selected for subsequent cardiogram segments to the precedent waveform data are different from each other.

24. A cardiogram waveform processing program according to claim 1, wherein the display control means simultaneously displays an output of a filter having a lowest cut-off frequency out of the waveform data or the first to the n th corrected waveform data correspondently with an output of a filter selected by the selecting means.

25. A cardiogram waveform processing program according to claim 1, wherein the selecting means recognizes an amount of variation of the base-line by calculating feature values of the waveform data or the corrected waveform data for each of the segments.

26. A cardiogram waveform processing program according to claim 25, wherein the selecting means uses a waveform value for at least one of a P-wave, a Q-wave, an R-wave, a S-wave, a ST-segment and a T-wave as the feature values.

27. A cardiogram waveform processing program according to claim 26, wherein the selecting means uses a waveform value of a point Pb or a waveform value of a point Qb as the feature values.

28. A cardiogram waveform processing program according to claim 26, wherein for larger differences between the waveform value and a reference value, the selecting means selects filtering means having a higher cut-off frequency.

29. A cardiogram waveform processing program according to claim 26, wherein the first cut-off frequency is a low cut-off frequency for performing functions of a cardiogram monitoring device defined in JIST 1304.

30. A cardiogram waveform processing program according to claim 25, wherein the cut-off frequency of the first to n th filters grows sequentially from the first filter, the second filter and up to the n th filter, and wherein the selecting means calculates an average of absolute values in difference between the first to the n th corrected waveform data for each of the plurality of segments as the feature value, and selects one of the filters in accordance with the averaged value in difference.

31. A cardiogram waveform processing program according to claim 30, wherein the display control means displays either an output of a filter having a lowest cut-off frequency out of the waveform data or the first to the n th corrected waveform data correspondently with an output of a filter selected by the selecting means in a simultaneous manner.

32. A cardiogram waveform processing program according to claim 31, wherein the selecting means carries out selection of a filter using the averaged difference values together with waveform values for at least one of a P-wave, a Q-wave, an R-wave, a S-wave, a ST-segment and a T-wave as a criterion of the selection.

33. A cardiogram waveform processing program according to claim 31, wherein the first to a fourth filter is provided each having a first to a fourth cut-off frequency, respectively.

34. A cardiogram waveform processing program according to claim 33, wherein the first cut-off frequency is a low cut frequency required by a cardiograph defined in JIST 1202, and wherein the second cut-off frequency is a low cut frequency required by a cardiogram monitoring device defined in JIST 1304.

35. A cardiogram waveform processing program according to claim 34, wherein the display control means controls so that the first corrected waveform data processed with the first cut-off frequency, the second corrected waveform data processed with the second cut-off frequency, the third corrected waveform data processed with the third cut-off frequency and the fourth corrected waveform data processed with the fourth cut-off frequency are displayed so that they are discriminable relative to one another.

36. A cardiogram waveform processing program according to claim 33, further comprising a fifth to a seventh filters each having a fifth to a seventh cut-off frequency, respectively.

37. A cardiogram waveform processing program according to claim 30, wherein the selecting means calculates average values of a first to an n−1 th for each of the plurality of segments of absolute values in difference between the first to the n−1 th corrected waveform data for each of the plurality of segments, and selects a filter having a lowest cut-off frequency among values having equal or less than a predetermined reference value in the average values of the first to the n−1 th.

38. A cardiogram waveform processing program according to claim 37, wherein the selecting means selects the n th filter when there is no value equal to or less than the predetermined reference value in the average values of the first to the n−1 th.

39. A cardiogram waveform processing program according to claim 25, further comprising feature value calculation means for supplemental use of diagnosing clinical conditions which calculates feature values for supplemental use of diagnosing clinical conditions for one of waveform data and corrected waveform data in each of the plurality of segments, wherein the display control means controls to display the feature values for supplemental use of diagnosing clinical conditions.

40. A cardiogram waveform processing program according to claim 39, wherein the display control means controls to display feature values for supplemental use of diagnosing clinical conditions in accordance with corrected waveform data processed by the filter selected with the selecting means, and further controls to carry out display for recognizing whether the feature values for supplemental use are based on corrected waveform data excessively restricting its base-line over a range defined in a corresponding JIS standard.

41. A cardiogram waveform processing program according to claim 1, wherein the first filtering means has a first cut-off frequency and the second filtering means has a higher cut-off frequency than the first cut-off frequency, and wherein the selecting means selects one of the first filtering means and the second filtering means.

42. A cardiogram waveform processing program according to claim 1, wherein the display control means controls to display a display object so that the display object belonging to, either: any one of the first corrected waveform data through the n th corrected waveform data, or any group of the first corrected waveform data through the n th corrected waveform data being grouped, is identifiably displayed corresponding to the displayed waveform.

43. A cardiogram waveform processing program according to claim 42, wherein the display control means controls to display a bar at a vicinity of the display waveform for each segment thereof, for recognizing whether or not the displayed waveform is corrected waveform data excessively restricting its base-line over a range defined in a corresponding JIS standard.

44. A cardiogram waveform processing program according to claim 1, wherein each of the plurality of segments represents one cardiac beat.

45. A cardiogram waveform processing program according to claim 44, wherein the display control means adjusts corrected waveform data so that the waveform data to be displayed sequentially, in accordance with tail waveform data behind a tail of T-wave preceding corrected waveform data, and corresponding tail waveform data in cardiogram segments preceding subsequent corrected waveform data, when continuity of the corrected waveform data to be displayed is lost because precedent waveform data selected for precedent cardiogram segments and subsequent corrected waveform data selected for subsequent cardiac segments to the precedent waveform data are different from each other.

46. A cardiogram waveform processing program executable to cause a computer to perform as a cardiogram waveform display device, the program including instructions stored on a non-transitory information storage media, the instructions controlling:

a first to an n th filtering means, for carrying out low frequency cut-off processing of waveform data which is converted to digital data from cardiogram waveform signals measured with a cardiograph;

selecting means for recognizing an amount of variation of a base-line for each of a plurality of segments relative to at least any one of the waveform data and the first to the n th corrected waveform data, and for selecting any one of the first to the n th filters in accordance with the amount of variation of the base-line for each of the segments; and display control means for displaying output of the filter selected for each of the segments by the selecting means.

47. A cardiogram waveform display device for selecting an appropriate filter for each one of a plurality of cardiac segments upon receipt of cardiogram waveform signals that were measured with a cardiograph, and for displaying output waveforms of the filter, wherein the cardiogram waveform display device either displays:

which one of a plurality of filters is selected for a corresponding to an output waveform for each one of a plurality of cardiac beats, or for filters grouped in a plurality of groups, which one of filters belonging to which group is selected, together with an output waveform of the selected filter for each cardiac beat.

48. A method of displaying cardiogram waveforms using a computer comprising the steps of:

generating waveform data by converting cardiogram waveform signals measured with a cardiograph to digital data;

carrying out low frequency cut-off processing at a first to an n th cut-off frequencies to the waveform data and performing a first to an n th filtering process to acquire a first to an n th corrected waveform data;

recognizing feature values representing variations of a base-line for each of a plurality of predetermined segments relative to any one of the waveform data and the first to the n th corrected waveform data; and selecting one of the first to the n th filters in accordance with the feature values and displaying output of the filter selected by the selecting means for each of the predetermined segments.

* * * * *